US 6,682,641 B1

(12) United States Patent
Finney et al.

(10) Patent No.: US 6,682,641 B1
(45) Date of Patent: Jan. 27, 2004

(54) ELECTROPHORESIS ASSEMBLY AND METHOD OF CASTING ELECTROPHORESIS GELS

(75) Inventors: Michael J. Finney, San Francisco, CA (US); Daniel E. Sullivan, Cambridge, MA (US); Bruce R. Turner, Exeter, NH (US); Alexis Vira, Somerville, MA (US); Peter B. Vander Horn, Foster City, CA (US); Charles P. Andre, San Francisco, CA (US); Sean Rubin, Mountain View, CA (US); Corey Nislow, San Francisco, CA (US); John R. Linton, Lincoln, MA (US); William D. Bowers, Peabody, MA (US)

(73) Assignee: MJ Research, Inc., Waltham, MA (US)

( * ) Notice: Subject to any disclaimer, the term of this patent is extended or adjusted under 35 U.S.C. 154(b) by 0 days.

(21) Appl. No.: 09/559,906

(22) Filed: Apr. 26, 2000

Related U.S. Application Data

(60) Provisional application No. 60/131,046, filed on Apr. 26, 1999, provisional application No. 60/131,525, filed on Apr. 29, 1999, and provisional application No. 60/151,722, filed on Aug. 31, 1999.

(51) Int. Cl.[7] .......................... B01D 57/02; B01D 59/42; B01D 59/50; B01D 61/42; B01D 61/58; C02F 1/469; C07K 1/26; C08F 2/58

(52) U.S. Cl. ...................... 204/466; 204/465; 204/606; 204/615; 204/616; 204/618; 204/619; 204/620; 425/179; 425/234; 425/543

(58) Field of Search ............................... 204/466, 465, 204/606, 615, 616, 618, 619, 620; 425/179, 234, 543

(56) References Cited

U.S. PATENT DOCUMENTS

| | | | | |
|---|---|---|---|---|
| 4,588,491 A | * | 5/1986 | Kreisher et al. ............. 204/620 |
| 4,693,804 A | * | 9/1987 | Serwer ....................... 204/466 |
| 4,915,811 A | * | 4/1990 | Yamamoto et al. ......... 204/619 |
| 4,929,329 A | * | 5/1990 | Danby et al. ............... 204/608 |
| 5,011,586 A | * | 4/1991 | Finney et al. ............... 204/466 |
| 5,112,470 A | * | 5/1992 | Sylvester .................... 204/618 |
| 5,164,065 A | * | 11/1992 | Bettencourt et al. ........ 204/619 |
| 5,304,292 A | * | 4/1994 | Jacobs et al. ............... 204/619 |
| 5,338,426 A | | 8/1994 | Shigeura et al. ............ 204/299 |
| 5,407,552 A | * | 4/1995 | Lebacq ....................... 204/619 |
| 5,447,679 A | | 9/1995 | Eigen et al. ................. 264/544 |
| 5,582,665 A | | 12/1996 | Eigen et al. .................. 156/69 |
| 5,938,906 A | * | 8/1999 | Moi et al. .................... 204/465 |
| 6,110,340 A | * | 8/2000 | Lau et al. .................... 204/467 |
| 6,340,123 B1 | * | 1/2002 | Lee et al. .................... 239/552 |

* cited by examiner

Primary Examiner—Jill Warden
Assistant Examiner—Jennine Brown
(74) Attorney, Agent, or Firm—Lahive & Cockfield, LLP

(57) ABSTRACT

The invention provides an electrophoresis cassette to cast electrophoresis gels and to separate and analyze molecular components by electrophoresis. The electrophoresis cassette comprises a top plate assembly, a spacer and a bottom plate. The top plate assembly is seated to the bottom plate with the spacer there between to define a thickness of the electrophoresis cassette and to seal an outer perimeter of the assembly. The top plate assembly includes a cathode reservoir connected to a first terminal end of a central plate, and an anode reservoir connected to a second terminal end of the central plate. When the electrophoresis cassette is assembled, the cathode and anode reservoirs are in alignment with the first and second terminal ends of the central plate to facilitate formation of leak-proof seals between the reservoirs and the assembly components. An embodiment of the invention provides a plurality of sample wells incorporated with the cathode reservoir and constructed of rigid, electrically non-conducting material to provide a hard-well sample loading site for uniform and consistent sample injection. Another embodiment provides a mechanical biasing system incorporated with a cathode reservoir body to bias the assembly components together. The invention also provides a method of casting electrophoresis gels with the electrophoresis cassette provided herein.

11 Claims, 13 Drawing Sheets

ELECTROPHORESIS ASSEMBLY AND METHOD OF CASTING ELECTROPHORESIS GELS

RELATED APPLICATIONS

The present application claims priority to U.S. Provisional Patent Application Ser. No. 60/131,046, filed on Apr. 26, 1999, U.S. Provisional Patent Application Ser. No. 60/131,525, filed on Apr. 29, 1999, and U.S. Provisional Patent Application Ser. No. 60/151,722, filed on Aug. 31, 1999, each of which is incorporated herein by reference.

FIELD OF THE INVENTION

The present invention relates to an apparatus for casting electrophoresis gels and performing electrophoresis for separation and analysis of DNA molecules, proteins and other charged molecules. The present invention also relates to a method of casting electrophoresis gels.

BACKGROUND OF THE INVENTION

Prior art electrophoresis assemblies include vertical and horizontal arrangements constructed of impermeable, non-conducting plates of glass or plastic between which electrophoresis gels are molded and contained during electrophoresis. Horizontal assemblies are less commonly used due to a number of inherent disadvantages and difficulties in casting, loading and electrophorescing horizontal gels. For instance, sample wells of horizontal assemblies that serve as sample loading sites are typically constructed of the same materials used to form gels. Sample wells are defined by molding well walls into a thickness of a gel. This molding technique is convenient and enables samples wells to be formed simultaneously with or immediately after the casting of gels. However, well walls formed of gel matrix materials contain the same electrolytic buffer ions as gels and are capable of conducting electrical current, which often results in problems with the introduction of samples into gels. When electrical current is applied to assemblies for sample injection, electrolytic buffer ions in well walls compete with similar ions in samples, causing the introduction of sample ions into gels to occur slowly. This effect produces broader sample peaks and limits the ability of the electrophoresis assemblies to resolve molecules of different sizes. In addition, well walls formed of gel materials are not mechanically reliable and susceptible to breakage and tearing during gel casting and sample loading.

Vertical electrophoresis assemblies well known in the art avoid problems associated with samples wells formed of gel materials by using non-conducting well dividers, often referred to as "shark's tooth combs", constructed of durable materials. A non-conducting comb, such as that disclosed in U.S. Pat. Nos. 4,883,577, 4,909,918 and 5,164,065, is inserted between the assembly plates and placed in a plane of a gel to provide a non-conducting, "hard well" sample loading site. Such non-conducting combs are difficult and inconvenient to insert between the plates of horizontal electrophoresis assemblies. When used in horizontal assemblies, such combs do not provide sample wells that are cable of containing samples by gravity. Therefore, sample wells of horizontal assemblies are invariably formed from gel materials and are electrically conductive.

Another disadvantage of horizontal assemblies is that they require external biasing mechanisms to maintain the assembly plates and buffer reservoirs in precise relationship during the casting and electrophorescing of gels. These biasing mechanisms are typically built with very high tolerances and require continual and difficult manual adjustment. Often external biasing systems work in conjunction with a base or other substrate, wherein the assembly plates and reservoirs are maintained in precise relationship by connection of the assembly components to the base. As disclosed in U.S. Pat. Nos. 5,137,613 and 5,228,971, a horizontal gel assembly is connected to a base by means of adjustable clamps. Uniform and effective biasing requires accurate and frequent manual adjustment of the clamps. In addition, since external pressure is required to cast gels in such a horizontal assembly, the assembly cannot be removed from its casting position in the base without the risk of the assembly coming apart.

The base disclosed in U.S. Pat. Nos. 5,137,613 and 5,228,971 also serves as a water jacket for temperature control of gel during electrophoresis. Such a water jacket cannot be constructed of a sufficiently transparent material to permit the use of photoinitiators, such as riboflavin or benzoin methyl ether, to initiate gel polymerization, and is limited to the use of chemical initiators. Chemically-initiated gel polymerization takes several hours, while photo-initiated gels polymerize in only a few minutes. In addition, the bases and water jackets as disclosed in U.S. Pat. Nos. 5,137,613 and 5,228,971 are expensive and difficult to manufacture.

Prior art horizontal assemblies are also prone to leak fluid from buffer reservoirs. In addition, horizontal assemblies are often not of sufficient size to accommodate various high performance electrophoretic techniques, such as DNA sequencing and DNA fragment size analysis. The technique of DNA sequencing and fragment analysis require longer electrophoresis assemblies on the order of 50 cm or longer. Longer horizontal assemblies require a greater number of amp-hours of electrophoretic current and, hence, a greater supply of buffer ions for a single electrophoretic run. Therefore, buffer reservoirs must be larger in horizontal assemblies used in these techniques to provide a sufficient supply of buffer ions to maintain a consistent electric current for the duration of an electrophoretic run. Buffer reservoirs of prior art horizontal assemblies as those disclosed in U.S. Pat. Nos. 5,137,613, 5,228,971 and 5,242,568, cannot be significantly enlarged without such designs becoming difficult to handle. In addition, such prior art buffer reservoirs are sealed only by means of gaskets, and an increase in reservoir size would render such buffer reservoirs more prone to leak fluid.

Therefore, it is desirable to provide a horizontal electrophoresis assembly for use in high performance electrophoretic techniques, such as DNA sequencing and DNA fragment analysis, that overcomes the limitations and disadvantages of prior art assemblies. It is desirable that the horizontal electrophoresis assembly include sample wells with well walls constructed of a durable and electrically non-conductive material to help ensure uniform and consistent sample injection into a gel. It is also desirable that the horizontal assembly is structured and constructed such that gels are optically accessible to permit photopolymerization and optical detection of separated molecules. The horizontal assembly that provides flexibility to increase the size of buffer reservoirs is also desirable. In addition, it is desirable that the structure and construction of the horizontal assembly facilitate formation of leak-proof seals between assembly components.

SUMMARY OF THE INVENTION

The invention provides an electrophoresis cassette to cast electrophoresis gels and to separate and analyze molecular components by electrophoresis. The invention also provides a method of casting electrophoresis gels.

A first embodiment of the invention includes an electrophoresis cassette comprising a top plate assembly seated on a bottom plate with a continuous spacer therebetween to define a thickness of the electrophoresis cassette and a molding space. The spacer seals an outer perimeter of the electrophoresis cassette.

The top plate assembly includes a central plate and a bottom plate, the bottom plate longer in length than the central plate. The central plate and the bottom plate are similarly rectangular in shape. The central plate has a first terminal edge or a cathode edge that is connected to a cathode buffer reservoir, and a second terminal edge or an anode edge that is connected to an debuffer reservoir. Side edges of the central plate are substantially covered by side rails that protect the side edges of the central plate during use. The side rails extend beyond the terminal ends of the central plate and connect with the side walls of the cathode and the anode buffer reservoirs to provide mechanical support to the top plate assembly.

The cathode buffer reservoir is a substantially rectangular receptacle of a sufficient depth to provide an adequate supply of buffer solution to maintain a consistent electrical current for the duration of an electrophoretic run. The cathode buffer reservoir includes a planar base connected to a body extending from the base to define the receptacle of the cathode buffer reservoir. The planar base includes a plurality of sample loading wells incorporated along a side wall of the planar base such that when the cathode buffer reservoir is connected to the cathode edge of the central plate the plurality of sample loading wells are positioned flush with the cathode edge.

The plurality of sample loading wells provides fluid communication between the cathode buffer reservoir and the molding space. The plurality of sample loading wells is defined by well walls that may be constructed of a suitable rigid, non-electrically conducting material. The well walls may include an upper terminal end that tapers to prevent sample dispensing equipment from impacting the well walls when dispensing samples into individual sample loading wells.

A mating comb is also provided in the first embodiment having a plurality of teeth or prongs. The teeth or prongs are similar in number, configuration and overall dimensions as the plurality of sample loading wells such that the mating comb is insertable into and fits flush with the plurality of sample loading wells.

The cathode buffer reservoir also includes an electrode that extends across the receptacle and provides electrical current to the cathode buffer reservoir from an external electrical source. The electrode is coupled within the cathode buffer reservoir. An electrode connector connects with the electrode and serves as a contact point for the external electrical source.

The anode buffer reservoir is a substantially rectangular receptacle of a sufficient depth to provide an adequate supply of buffer solution to maintain a consistent electrical current for the duration of an electrophoretic run. The anode buffer reservoir includes a substantially planar base. A through slot is disposed substantially centrally in the planar base. A channel is defined by the planar base and between the through slot and a side wall of the anode buffer reservoir proximate to the central plate, and is in fluid communication with the through side. The channel is also in fluid communication with an opening in the side wall. The opening is raised upward from a bottom of the side wall more than the thickness of an electrophoretic gel and less than the height of the central plate. In addition, the opening is in fluid communication with the molding space between the central plate and the bottom plate when the electrophoresis cassette is assembled.

The side wall encloses the anode buffer reservoir such that the central plate is not required to act as a fourth wall to form the receptacle of the anode buffer reservoir. The side wall includes protrusions. The protrusions increase a volume of the receptacle of the anode buffer reservoir and increase the surface area available to connect the anode buffer reservoir the central plate. The protrusions also add support for the anode buffer reservoir when the electrophoresis cassette is assembled.

The anode buffer reservoir also includes an electrode that extends across the receptacle and provides electrical current to the anode buffer reservoir from an external electrical source. The electrode is coupled within the anode buffer reservoir. An electrode connector connects with the electrode and serves as a contact point for the external electrical source.

The cathode buffer reservoir, the central plate, the anode buffer reservoir and the side rails are assembled to form the top plate assembly. The components may be adhesively connected such that the cathode buffer reservoir is adhesively connected at the cathode edge of the central plate and the anode buffer reservoir is adhesively connected to the anode edge of the central plate. Similarly, the side rails may be adhesively connected to the side edges of the central plate.

The bottom plate of the electrophoresis cassette has a length to accommodate the length of the central plate plus a width of the cathode buffer reservoir and a width of the anode buffer reservoir. The spacer is a continuous frame-type configuration seated on a top surface of the bottom plate substantially adjacent to a perimeter edge of the bottom plate. The spacer, the bottom plate and the central plate define the molding space and the thickness of the electrophoresis cassette.

The bottom surface of the central plate and the top surface of the bottom plate are substantially uniform and parallel. In addition, the spacer has a substantially uniform surface. The substantially uniform and parallel surfaces of the central plate and the bottom plate, and the substantially uniform surface of the spacer help to ensure a uniform thickness of an electrophoresis gel cast in the molding space.

To assemble electrophoresis cassette, the spacer is seated on the top surface of the bottom plate and the top plate assembly is seated on a top surface of the spacer and the top surface of the bottom plate. The assembled components are held in close proximity and alignment by clamping mechanisms, such as binder clamps, or other fasteners well known in the art.

To cast an electrophoretic gel, the electrophoresis cassette is assembled as described above. Flowable gel material suitable for molding an electrophoretic gel, such as a gel solution, is poured or injected into the anode buffer reservoir. The gel solution flows into and substantially fills the through slot, the channel and the opening of the anode buffer reservoir. The gel solution also flows beneath the anode buffer reservoir and substantially fills an area defined by a bottom surface of the anode buffer reservoir, the spacer and the top surface of the bottom plate. From the through channel, the gel solution flows into and substantially fills the molding space defined by the central plate, the spacer and the bottom plate. The gel solution flows from the molding space and into the plurality of sample loading wells and substantially fills individual sample wells. The gel solutions also flows beneath the cathode buffer reservoir and substantially fills an area defined by a bottom surface of the cathode buffer reservoir, the spacer and the top surface of the bottom plate.

The mating comb is placed in the plurality of sample loading wells to substantially displace the gel solution therein. The mating comb remains in the plurality of sample loading wells until the gel solution polymerizes. After polymerization, the mating comb is removed and individual sample loading wells are gel-free and ready for sample loading.

Thin layers of polymerized gel seal the area between the cathode buffer reservoir and the bottom plate. Thin layers of polymerized gel also seal the plurality of sample loading wells with the cathode edge of the central plate. The area beneath the anode buffer reservoir contains thin layers of polymerized gel to seal the anode buffer reservoir with the bottom plate. The through slot, the channel and the opening are substantially filled with polymerized gel to seal the anode buffer reservoir and the anode edge of the central plate. The contiguous nature of the polymerized gel forms leak-proof seals.

Upon completion of gel casting, electrophoresis of samples may proceed. The cathode buffer reservoir is filled with distilled water or a dilute salt solution to serve as a sample injection solution. The anode buffer reservoir is filled with electrolytic buffer solution of an appropriate concentration. Samples are dispensed into the plurality of sample loading wells either manually or with automated dispensing equipment. The samples are injected into the electrophoresis gel by application of a brief pulse of high voltage electrical current to the cathode buffer. The sample injection solution contained in the cathode buffer reservoir is replaced with an electrolytic buffer of an appropriate concentration. Electrical current to conduct electrophoresis is supplied by an external electrical source. Temperature control of the electrophoresis gel is supplied by a temperature control mechanism.

A second embodiment of the invention includes similar components as the electrophoresis cassette of the first embodiment except that the plurality of sample loading wells comprises a plurality of through holes machined or molded in a surface of the planar base of the cathode buffer reservoir. The plurality of through holes is positioned substantially adjacent to the side wall of the cathode buffer reservoir that is positioned flush with the cathode edge of the central plate when the electrophoretic cassette is assembled. A mating comb is provided with a plurality of teeth or prongs that are similar in number, configuration and overall dimensions as the plurality of through holes such that the mating comb is insertable into and fits flush with the plurality of through holes. Although the through holes may be of any configuration and shape, the plurality of through holes of the second embodiment are circular cylinders to facilitate ease in manufacture.

A third embodiment of the invention includes similar components as the electrophoresis cassette of the first embodiment except that the plurality of sample loading wells is arranged as staggered dual parallel linear arrays of through holes. Individual through holes of a first linear array are staggered and parallel in relation to individual through holes of a second linear array. The staggered arrangement of parallel linear arrays of through holes acts to spatially stagger sample loading to effect the technique of sample lane identification or lane tracking that is typically achieved by temporally staggering the injection of samples into the electrophoresis gel. Individual through holes may be configured as circular cylinders which permits ease in manufacturing.

A fourth embodiment of the invention provides an electrophoresis cassette similar to the electrophoresis cassette of the first embodiment except that a cathode buffer reservoir, an anode buffer reservoir and a central plate are not permanently joined into a single assembly, but rather are held together by a mechanical biasing system. The mechanical biasing system holds and maintains components of the electrophoresis cassette of the fourth embodiment in close proximity and alignment during gel casting and electrophoresis. Individual through holes of the fourth embodiment may be circular cylinders to permit manufacturing ease.

The cathode buffer reservoir includes a body and a base perimeter. The body includes a bottom planar surface with a plurality of sample loading wells incorporated with a side wall of the bottom planar surface. The body traverses the central plate and has a width equal to a length of the central plate. The body includes the mechanical biasing system that comprises spring-biased slide blocks positioned at end portions of the body for mechanically biasing the cathode edge of the central plate flush against the plurality of sample loading wells when the electrophoresis cassette is being assembled. The body also includes locating pins that downwardly protrude from the end portions to facilitate positioning of the cathode buffer reservoir relative to the bottom plate.

The base perimeter is constructed in a U-shaped configuration and is substantially flat and uniform. The base perimeter traverses the central plate and has a length substantially equal to the width of the body. The base perimeter is adhesively connected to the top surface of the central plate and positioned on the central plate such that end portions of the U-shaped configuration terminate in flush alignment with the cathode edge of the central plate. The end portions also include reference point protrusions that extend laterally at the end portions of the base perimeter to ensure the end portions are in consistent alignment with the cathode edge.

The anode buffer reservoir is substantially similar in structure and construction as the anode buffer reservoir of the first embodiment except that the anode buffer reservoir in the fourth embodiment includes locating pins that downwardly protrude from end portions of the anode buffer reservoir. The locating pins are positioned on the anode buffer reservoir in alignment with side edges of the central plate.

The anode buffer also includes a channel in a lower section of side wall of the anode buffer reservoir defined by the bottom plate and between a through slot and an opening in the side wall. The through slot is positioned substantially off-center in a planar base of the anode reservoir and substantially adjacent to the channel such that the through slot and the channel are in fluid communication. The channel is in fluid communication with the opening in the side wall. The opening is raised upward from a bottom of the first side wall more than a thickness of an electrophoretic gel contained in the electrophoresis cassette and less than the height of the central plate. The channel is positioned between the anode edge of the central plate and the through slot when the electrophoresis cassette is assembled.

The anode buffer reservoir also includes a gasket connected to are outer surface of the side wall of the anode buffer reservoir proximate to the central plate to effect a seal between the anode buffer reservoir and the anode edge of the central plate.

The spacer and the bottom plate are substantially similar in structure and construction to the spacer and the bottom plate of the first embodiment except that the spacer and the bottom plate in the fourth embodiment include features to receive the locating pins of the cathode buffer reservoir and the anode buffer reservoir. The spacer includes notches at approximately each corner to receive the locating pins of the buffer reservoirs. The bottom plate includes slots located approximately adjacent to each corner along side edges. The notches of the spacer and the slots of the bottom plate are in longitudinal alignment such that during assembly of the electrophoresis cassette the locating pins of the cathode and anode buffer reservoirs are received by the notches of the spacer and subsequently received by the slots of the bottom plate.

The electrophoresis cassette of the fourth embodiment is assembled by seating the spacer on a top surface of the bottom plate and inserting the locating pins of the cathode buffer reservoir through the notches of the spacer and into the slots of the bottom plate. The central plate with the base perimeter facing upward is seated on a top surface of the spacer. The cathode edge of the central plate is positioned flush with the plurality of sample loading wells of the body of the cathode reservoir buffer. The central plate is manually forced against the body of the cathode reservoir buffer which compresses the spring-biasing mechanisms positioned in the body of the cathode reservoir buffer, enabling the cathode edge to make firm contact with the plurality of sample loading wells. In addition, the end portions of the base perimeter are flush against and compress gaskets located at the end portions of the body of the cathode buffer reservoir to achieve leak-proof seals. The anode buffer reservoir is subsequently seated on the top surface of the spacer at the anode edge of the central plate by inserting the locating pins of the anode buffer reservoir through the notches of the spacer and into the slots of the bottom plate. When the anode buffer reservoir is connected to the bottom plate and positioned flush with the anode edge, the central plate is manually released. The spring-biasing mechanisms expand, compressing the central plate and the bottom plate between the cathode and anode buffer reservoirs, and compressing the central plate downwardly against the spacer and the bottom plate.

The electrophoretic cassette of the fourth embodiment is similarly used to cast electrophoretic gels according to the method of the first embodiment. Sample injection and electrophoresis proceed as described in the first embodiment.

A fifth embodiment of the invention includes a clamping/assembling fixture suitable for use in assembling any of the electrophoresis cassettes of the previous embodiments. The clamping/assembling fixture is a frame-type configuration with a length and a width slightly larger than the width of the electrophoresis cassettes. A plurality of fasteners is positioned on at least three sides of the clamping/assembling fixture to hold the central plate, the spacer and the bottom plate, and optionally at least one buffer reservoir, in close proximity and alignment.

A sixth embodiment of the invention includes an electrophoresic cassette similar to the electrophoresis cassette of the first embodiment except that a modified spacer with a U-shaped frame, a cathode blank and a mechanical biasing system are employed. The modified U-shaped spacer is seated on the top surface of the bottom plate such that a continuous portion of the modified spacer is under the anode buffer reservoir and end portions of the spacer terminate on the top surface of the bottom plate at a position flush with the cathode buffer reservoir.

The cathode blank replaces the cathode buffer reservoir during gel casting and substantially fills a space on the top surface of the bottom plate occupied by the cathode buffer reservoir. The cathode blank acts as a template to restrict flow of the gel solution to the cathode edge of the central plate. The central plate, the modified U-shaped spacer, the bottom plate and the cathode blank define a molding space. The cathode blank is removed and replaced with the cathode buffer reservoir after completion of gel casting. The cathode buffer reservoir is positioned flush with the cathode edge of the central plate.

The mechanical biasing system includes systems such as those disclosed in U.S. Pat. Nos. 5,242,568, 5,228,971 and 5,137,613, incorporated herein by reference. The mechanical biasing system holds and maintains assembly components in close proximity and alignment during gel casting and electrophoresis. The mechanical biasing system biases the cathode buffer reservoir against the cathode edge of the central plate to position the plurality of sample loading wells flush with the cathode edge. The mechanical biasing system similarly biases the anode buffer reservoir against the central plate to position the anode buffer reservoir flush with the anode edge of the central plate. In addition, the mechanical biasing system ensures downward biasing of the central plate against the spacer and the bottom plate.

The electrophoresis cassette of the sixth embodiment is used to cast an electrophoretic gel according to the method of the first embodiment except that the modified U-shaped spacer and the cathode blank are employed during gel casting. The molding space defined by the bottom plate, the modified U-shaped spacer, the central plate and the cathode blank substantially fills with the gel solution. After polymerization, the cathode blank is removed. The electrophoretic gel polymerized in the molding space terminates in flush alignment with the cathode edge of the central plate. The cathode buffer reservoir is seated on the top surface of the bottom plate with the plurality of sample loading wells positioned flush with the cathode edge and a terminal edge of the electrophoretic gel. Sample injection and electrophoresis then proceed as described in the first embodiment.

A seventh embodiment of the invention includes an electrophoresis cassette similar to the electrophoresis cassette of the sixth embodiment except that the cathode blank and the modified U-shaped spacer are not used. A spacer with a continuous frame-type configuration is employed and seated on the top surface of the bottom plate. The cathode buffer reservoir is seated on a top surface of the spacer and includes recesses on a bottom surface. The recesses have approximately the same width and depth as the spacer and are positioned on the bottom surface of the cathode buffer reservoir in direct alignment with the spacer. When the cathode buffer reservoir is seated on the top surface of the spacer, the recesses receive portions of the spacer on which the cathode buffer reservoir is seated. This arrangement permits the cathode buffer reservoir to be seated substantially flush with the top surface of the bottom plate.

The electrophoresis cassette of the seventh embodiment is used to cast an electrophoretic gel according to the method of the first embodiment except that the cathode buffer reservoir with the recesses as described above is employed. The gel solution is substantially prevented from flowing into an area under the cathode buffer reservoir, although extremely small amounts of the gel solution permeate under and into the area under the cathode buffer reservoir. Polymerization of small amounts of gel solution seal the bottom of the cathode buffer reservoir to the top of the bottom plate. Sample injection and electrophoresis then proceed as described in the first embodiment.

BRIEF DESCRIPTION OF THE DRAWINGS

For a better understanding of the present invention, reference is made to the drawings provided below, which are incorporated herein by reference and in which.

DETAILED DESCRIPTION OF THE INVENTION

Illustrative embodiments of the invention described below are directed to an electrophoresis cassette to cast a variety of electrophoresis gels and to separate and analyze molecular components by electrophoresis. More particularly, embodiments of the invention include a horizontal electrophoresis cassette of use in the techniques of DNA sequencing and DNA fragment analysis. However, those of ordinary skill in the art will appreciate that embodiments in accordance with the invention are not limited to horizontal electrophoresis cassettes, but rather, may be used in vertical cassette arrangements and with a variety of separation and detection techniques. Illustrative embodiments are also directed to a method of casting electrophoresis gels.

Embodiments of the invention will be described with reference to FIGS. 1 through 14 which are presented herein for the purpose of illustration are not intended to limit the scope of the invention.

Figure 1:
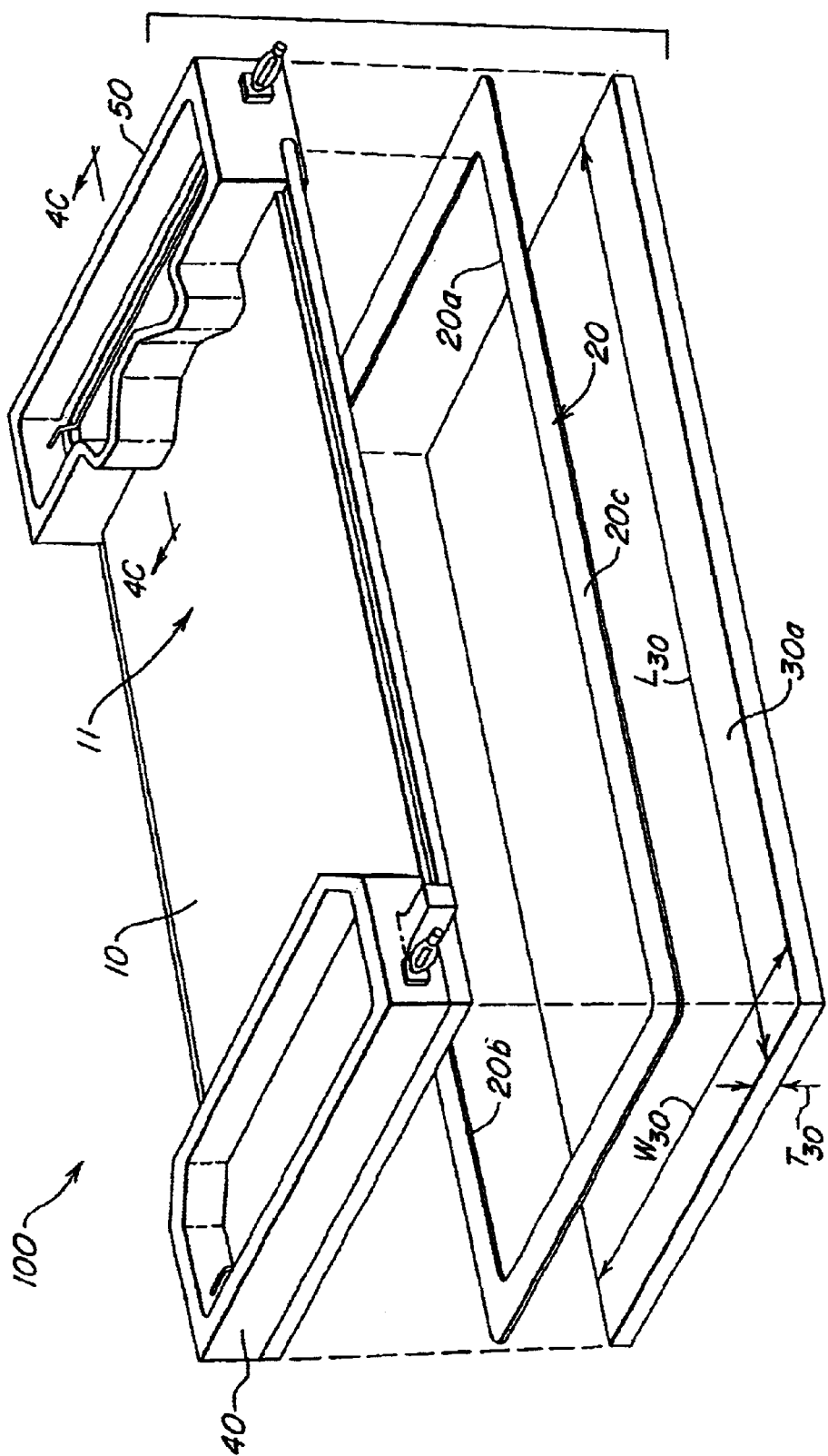
FIG. 1 is an exploded perspective of an electrophoresis cassette of a first embodiment of the invention.

FIGS. 1–4c refer to a first embodiment of the invention that provides an electrophoresis cassette 100 for casting gels and electrophoresing samples. As illustrated in FIG. 1, the electrophoresis cassette 100 comprises a top plate assembly 10, a spacer 20 and a bottom plate 30. The top plate assembly 10 is mounted to the bottom plate 30 with the spacer 20 incorporated therebetween to define the thickness of the electrophoresis cassette and to seal an outer perimeter of the cassette 100. As will become apparent from the description provided below, the components 10, 20, 30 of the electrophoresis cassette 100 are structured and configured to provide ease in assembly and to facilitate the formation of leak-proof seals between the components when assembled to form the cassette 100.

Figure 2:
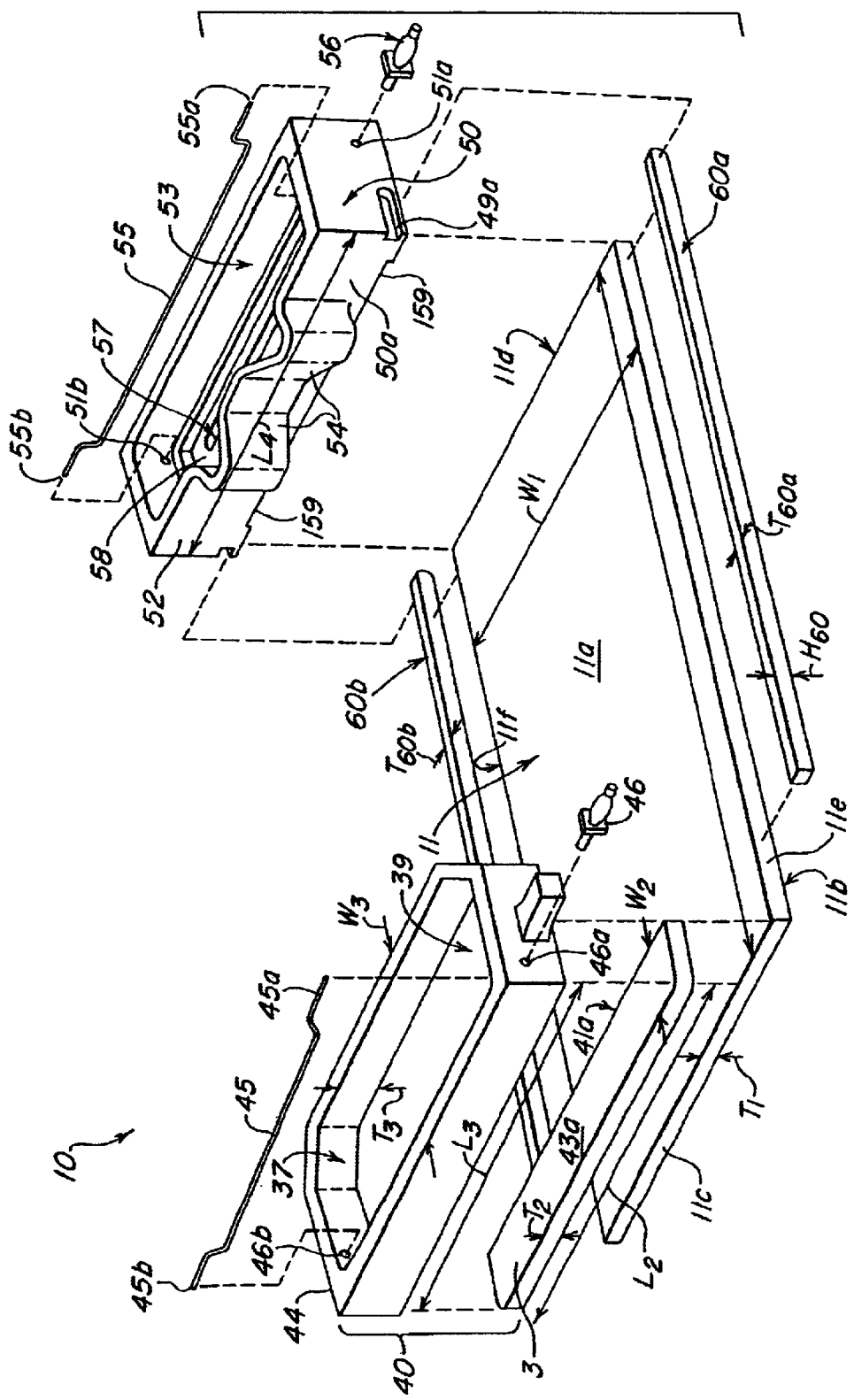
FIG. 2 is an exploded perspective of a top plate assembly of the first embodiment.

As shown in FIG. 2, the top plate assembly 10 comprises a central plate 11. The central plate 11 is made of a suitable rigid material capable of withstanding the conditions of electrophoresis, such as, but not limited to, glass, alumina ceramic or glass-filled epoxy. In the first embodiment shown in FIGS. 1–4c, the central plate 11 is constructed of glass. Glass is a desirable material of construction because it is electrically non-conductive and may be ground and polished to specific surface tolerances. Glass also permits visual observation and inspection of gels during casting. In the event separated molecules are to be optically detected, the central plate 11 is constructed of glass with low fluorescence characteristics, such as BK7 glass or Borofloat glass, available from Schott Corporation of Yonkers, N.Y.

The central plate 11, when made from Borofloat glass, has a length $L_1$ of from about 30 cm to about 65 cm, a width $W_1$ of from about 20 cm to about 30 cm, and a thickness $T_1$ from about 5 mm to about 8 mm, depending upon a desired number of samples and a desired electrophoresis separation distance. As illustrated, the central plate 11 is rectangular, although the configuration of the central plate 11 of the invention is not limited to this shape or the specified dimensions.

The central plate 11 includes a top surface 11a and a bottom surface 11b. The top and bottom surfaces 11a, 11b of the central plate do not contain slots, holes or other internal machining and are polished to a flatness of about 1 µm per inch to ensure top and bottom surfaces 11a, 11b are substantially uniform and parallel. Uniformity of the bottom surface 11b is helpful for casting electrophoretic gels of uniform thickness. Parallel top and bottom surfaces 11a, 11b helps ensure the proper alignment and focusing of the electrophoresis cassette 100 for optical reading.

The assembly 10 also includes a cathode buffer reservoir 40, an anode buffer reservoir 50 and a pair of side rails 60a, 60b. The central plate 11 includes a first terminal edge, or a cathode edge 11c, and a second terminal edge, or anode edge 11d, extending the width $W_1$ of the central plate 11. The cathode buffer reservoir 40 is adhesively joined to the central plate 11 at the cathode edge 11c, and the anode buffer reservoir 50 is adhesively joined with the central plate 11 at the anode edge 11d. The side rails 60a, 60b are adhesively attached to and cover a first and a second side edge 11e, 11f, respectively, of the central plate 11. The side rails 60a, 60b are of sufficient length to overlap and connect with an external surface of side walls of the cathode and anode buffer reservoirs 40, 50 when the reservoirs are joined with the central plate 11.

The cathode and anode edges 11c, 11d are polished to a flatness of about 5 µm. The finish helps to facilitate effective joining and adhering of the cathode and anode buffer reservoirs 40, 50 to the central plate 11. Suitable adhesives, such as, but not limited to, acrylic and epoxy adhesives may be used. In the first embodiment, epoxy adhesive is used due to its chemical resistance and low water absorption capacities.

The cathode and anode buffer reservoirs 40, 50 contain and provide ions required to conduct electrical current to the electrophoresis cassette 100 during electrophoresis. The cathode and anode buffer reservoirs 40, 50 may contain solid materials, such as ion exchange resins, or alternatively, may contain electrolytic buffers. In the first embodiment, the cathode and anode buffer reservoirs 40, 50 contain electrolytic buffers similar in composition to electrolytes comprising gels contained by the electrophoresis cassette. The cathode and anode buffer reservoirs 40, 50 are of sufficient size to contain an adequate volume of electrolytic solution to provide a sufficient supply of ions to maintain a consistent electrical current for the duration of an electrophoretic run.

The cathode buffer reservoir 40 is a substantially rectangular receptacle 39 for containing electrolytic buffers and also serves as a sample loading site of the electrophoresis cassette 100. As shown in FIGS. 1 and 2, the cathode buffer reservoir 40 includes a planar cathode reservoir base 43, a cathode reservoir body 44, an electrode 45 and an electrical connector 46. The cathode reservoir base 43 includes a substantially planar top surface 43a and is substantially rectangularly shaped. The cathode reservoir base 43 has a length $L_2$ and a thickness $T_2$ approximately equal to the width $W_1$ and the thickness $T_1$, respectively, of the central plate 11.

The cathode reservoir base 43 is adhesively joined the cathode reservoir body 44 to form the cathode buffer reservoir 40. The cathode reservoir body 44 has a length $L_3$ approximately equal to the width $W_1$ of the central plate 11 and substantially similar to the length $L_2$ of the cathode reservoir base 43. The body 44 has a width $W_3$ that is wider than a width $W_2$ of the cathode reservoir base 43 and extends over the central plate 11, adding strength to the assembly 10. A thickness or depth $T_3$ of the cathode reservoir body 44 is sufficiently large such that when the reservoir 40 is connected to the central plate 11, the receptacle 39 is enclosed except for a top opening. The receptacle 39 is of an adequate size to contain a sufficient volume of electrolytic buffer. The cathode reservoir body 44 traverses the cathode reservoir base 43 and the central plate 11 to add strength to the top plate assembly 10.

Figure 3:
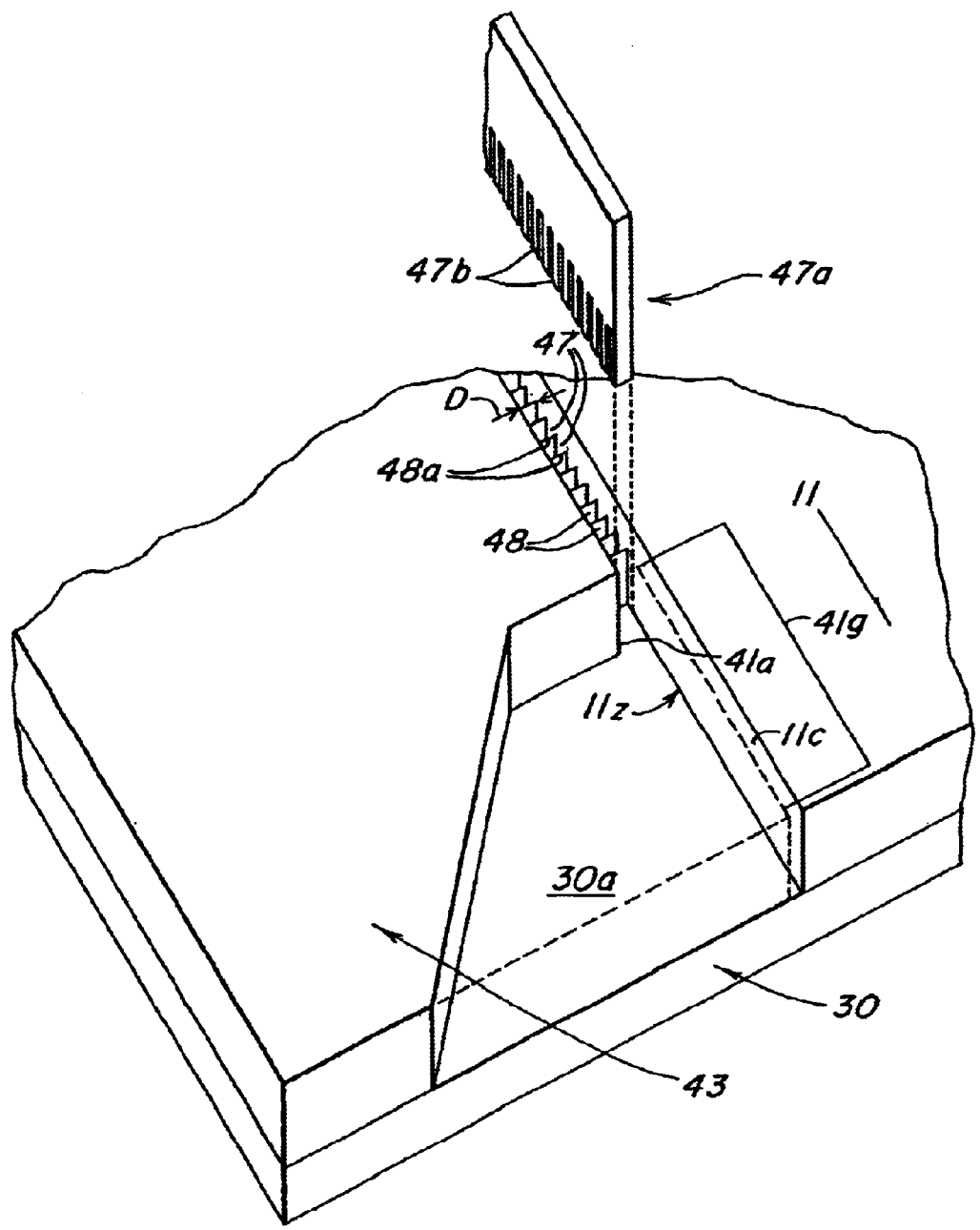
FIG. 3 is a cross-sectional perspective of a planar base of a cathode buffer reservoir and a plurality of sample load wells of the electrophoresis cassette of the first embodiment.

As shown in FIG. 3, the cathode reservoir base 43 includes a plurality of sample loading wells 47 arranged in a linear array and incorporated with the surface 41a. Individual sample loading wells 47 are defined by well walls 48 having a height of at least approximately 7 mm, such as the thickness of the central plate 11. Well walls 48 have a thickness of from about 0.25 mm to about 1 mm, although they may be more narrowly constructed depending upon the strength and stiffness of the material used to construct the well walls 48. Individual sample loading wells 47 have a longitudinal depth D, e.g., of from about 1 mm to about 2 mm to help with introduction of samples either manually or with automated dispensing equipment into individual sample loading wells 47. The well walls 48 may also include an upper terminal end 48a that is tapered to prevent dispensing equipment, such as pipetting devices, from impacting well walls 48 when such devices dispense sample volumes into individual sample loading wells 47.

When the electrophoresis cassette 100 is assembled, the plurality of sample loading wells 47 is positioned flush with the cathode edge 11c, as shown in FIG. 3. A uniform interface between the plurality of sample loading wells 47 and a point of intersection 11z of the bottom surface 11b and the cathode edge 11c of the central plate 11, is substantially achieved. The uniform interface helps to ensure consistent electrophoretic injection of sample molecules into electrophoretic gels.

The cathode reservoir base 43 is constructed of a suitable material capable of withstanding the conditions of electrophoresis, such as, but not limited to, rigid materials including glass-filled epoxy, to form a plurality of "hard well" sample loading wells. Alternatively, the cathode reservoir base 43 may be constructed of resilient materials including polyethlene or silicone rubber. In the first embodiment, the cathode reservoir base is constructed of glass-filled epoxy to form a "hard-well" cathode reservoir base 43.

The cathode reservoir base 43 and the cathode reservoir body 44 are adhesively connected to form the cathode buffer reservoir 40. The cathode buffer reservoir 40 is adhesively joined with the cathode edge 11c of the central plate 11. In the first embodiment, as shown in FIG. 3, epoxy adhesive is applied to a section 41g of the front side wall 41a (shown in phantom) that is free of the plurality of sample loading wells 47. In addition, epoxy adhesive may be applied to a front surface of individual well walls 48 to adhere the plurality of sample loading wells 47 to the cathode edge 11c to help ensure formation of a leak-proof seal between the cathode buffer reservoir 40 and the central plate 11.

A mating comb 47a includes a plurality of teeth 47b arranged in a linear array. The teeth or prongs 47b of the mating comb 47a correspond in number and configuration to the plurality of sample loading wells 47 of the cathode reservoir base 43 such that the teeth 47b of the mating comb 47a are insertable into and closely fit flush with the well walls 48 of the sample loading wells 47. The teeth or prongs 47b are of sufficient length that when the mating comb 47a is inserted into the plurality of sample loading wells 47, the teeth 47b protrude through bottoms of the sample loading wells 47. The teeth 47b protrude a length of approximately equal to a thickness of the spacer 20 to meet a top surface 30a of the bottom plate 30.

The mating comb 47a is inserted into the plurality of sample loading wells 47 during gel casting to effectively displace gel solution and to prevent polymerization of gel solution in sample loading wells. The mating comb 47a is constructed of a suitable material, such as acrylic plastic, which has a slight inhibitory effect on polymerization of gels immediately adjacent to a surface of the mating comb. After gel casting and polymerization, the mating comb 47a is removed from the plurality of sample loading wells 47. Individual sample wells are gel-free and ready to accept samples.

The cathode buffer reservoir 40 also includes a cathode electrode 45. The cathode electrode 45 is an elongated electrode extending across the receptacle 39 of the cathode buffer reservoir 40, traversing a length of the cathode buffer reservoir above the cathode reservoir base 43. The cathode electrode 45 has a first terminal end 45a and a second terminal end 45b. A mounting fixture 46b receives the second terminal end 45b. The first terminal end 45a is received by a through hole 46a bored through the end of the cathode reservoir body 44. An electrode connector 46 is correspondingly mounted to the through hole 46a at an outer surface to receive and couple with the first terminal end 45a of the provide electrical current to the cathode buffer reservoir 40 during electrophoresis.

As shown in FIG. 2, the anode buffer reservoir 50 provides a substantially rectangular receptacle 53 that includes a body 52, a substantially planar base 58, an electrode 55 and an electrical connector 56.

The body 52 has a length $L_4$ approximately equal to the width $W_1$ of the central plate 11 plus thicknesses of the rails 60a, 60b. The body 52 provides the receptacle 53 with a sufficient depth to form the reservoir 40 of sufficient size to contain an adequate volume of electrolytic buffer.

A first side wall 50a of the anode buffer reservoir 50 includes protrusions 54, as shown in FIGS. 1 and 2, that extend over the top surface 11a of the central plate 11 when the anode buffer reservoir 50 is joined with the central plate 11. The overlapping protrusions 54 serve to increase surface area available for adhesively joining the anode buffer reservoir 50 to the central plate 11. The increased surface area also adds support for the anode buffer reservoir 50 when mounted to the central plate 11. The protrusions 54 also provide a larger receptacle 53 than if the body 52 had straight walls.

The anode buffer reservoir 50 is constructed of suitable rigid material, capable of withstanding the conditions of electrophoresis, such as, but not limited to, glass-filled epoxy. As described above, the anode buffer reservoir 50 is adhesively joined to the central plate 11 for assembly of the electrophoresis cassette 100. In the first embodiment, adhesive is applied along a section of body 52 below the protrusions 54 to adhesively join the anode buffer reservoir 50 to the anode edge 11d of the central plate 11. A suitable adhesive capable of withstanding the conditions of electrophoresis, such as, but not limited to, Extreme-Katiobond 1052 available from Extreme Adhesives of Seabrook, N.H., may be used. The polished uniform surface of the anode edge 11d facilitates a uniform interface between the body 52 of the anode buffer reservoir and the anode end 11d of the central plate 11 to form a leak-proof seal.

As shown in FIGS. 2 and 4a–4c, the planar base 58 of the anode buffer reservoir 50 includes an elongated through slot 57 disposed approximately centrally in the planar base 58. The length of the through slot 57 is less than the distance between inner edges 20a, 20b of the spacer 20, as shown in FIG. 1, to guard against the through slot 57 overlapping with the spacer when the top plate assembly 10 is joined with the spacer 20 and the bottom plate 30 to form the electrophoresis cassette 100.

Figure 4A:
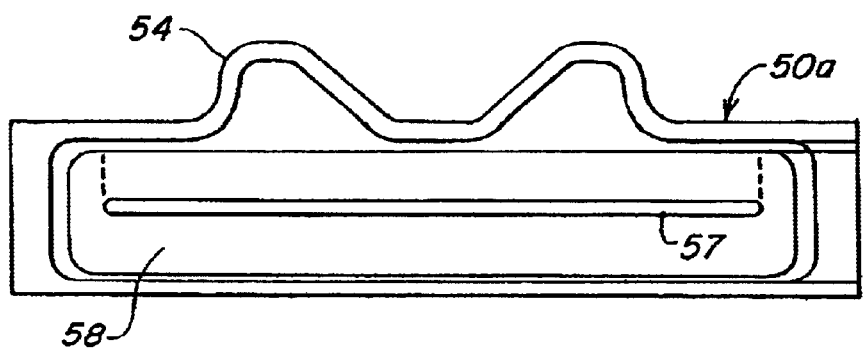
FIG. 4a is a top view of anode buffer reservoir of the first embodiment.
Figure 4B:
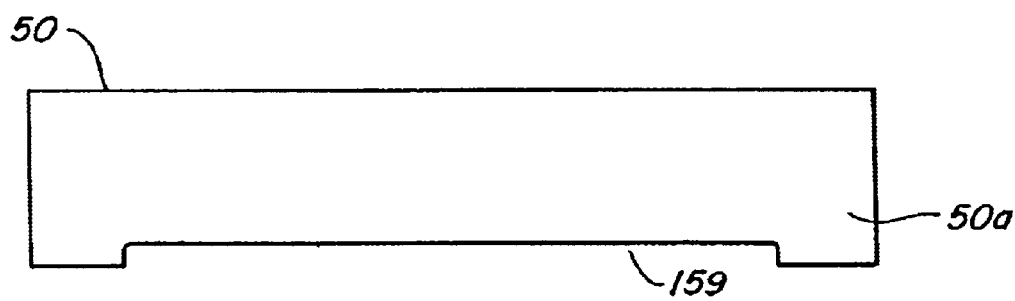
FIG. 4b is a front view of the anode buffer reservoir of the first embodiment.
Figure 4C:
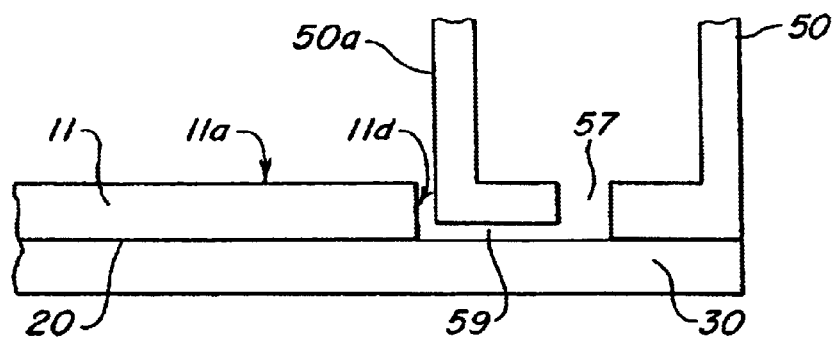
FIG. 4c is a cross-sectional side view of the anode buffer reservoir incorporated with the electrophoresis cassette of the first embodiment.

As shown in FIGS. 4b and 4c, a channel 59 is defined the base 58 by the bottom plate 30 and between the through slot 57 and the first side wall 50a. The channel 59 is in fluid communication with an opening 159 in the first side wall 50a of the anode buffer reservoir 50, as shown in FIG. 4b. The opening 159 is raised upward from a bottom of the first side wall 50a more than a thickness of an electrophoretic gel contained in the electrophoresis cassette 100 and less than the height of the central plate 11. FIG. 4c shows a cross-sectional side view of the anode buffer reservoir 50 when assembled with the central plate 11 and the bottom plate 30. The channel 59 is positioned between the anode edge 11d of the central plate 11 and the through slot 57.

Referring to FIG. 2, the proximal side wall 50a of the anode buffer reservoir 50 encloses the anode buffer reservoir 50 such that it is not needed to use the central plate 11 as a fourth wall to form the anode buffer reservoir, as many prior art devices require. This structure and arrangement permits an entire gel-containing volume to be optically accessible through the bottom plate 30. Such accessibility permits the gel to be photopolymerized through the bottom plate 30.

The anode buffer reservoir 50 also includes an anode electrode 55 similar to the cathode electrode 45. The anode electrode 55 is an elongated electrode disposed within the receptacle portion 53 of the anode buffer reservoir 50, traversing a length of the anode buffer reservoir 50 above the planar base 58. The anode electrode has a first terminal end 55a and a second terminal end 55b. A mounting fixture 51b receives the second terminal end 55b. The first terminal end 55a is received by a through hole 51a bored through the anode buffer reservoir 50. An electrode connector 56 is correspondingly mounted to the reservoir 50 about the through hole 51a to receive and couple with the first terminal end 55a of the anode electrode. The electrode connector 56 is connected to an electrical supply to provide electrical current to the anode buffer reservoir 50 during electrophoresis.

As shown in FIGS. 1 and 2, the top plate assembly 10 of the first embodiment also includes the pair of side rails 60a, 60b. The side rail 60a is attached to a side edge 11e of the central plate 11 and the second side rail 60b is attached to a side edge 11f. The side rails 60a, 60b are adhesively attached to the side edges 11e, 11f with a suitable adhesive, such as, but not limited to, acrylic or epoxy adhesive. The side rails 60a, 60b are of a height $H_{60}$ that is slightly less than the thickness $T_1$ of the central plate 11. The side rails 60a, 60b cover and protect the first and second side edges 11e, 11f from damage during use. The side rails 60a, 60b overlap and connect with the base 43 of the cathode buffer reservoir 40 and are received in slots 49a, 49b in the anode buffer reservoir to provide mechanical support to the top plate assembly 10. The side rails 60a, 60b are constructed of suitable rigid material capable of withstanding the conditions of electrophoresis, such as, but not limited to, glass-filled epoxy.

As described above and shown in FIG. 2, the cathode buffer reservoir 40, the anode buffer reservoir 50 and the side rails 60a, 60b are assembled to form the top plate assembly 10. The top plate assembly 10 is joined with the spacer 20 and the bottom plate 30 to create the electrophoresis cassette 100.

The bottom plate 30 has a similar configuration to the central plate 11, as shown in FIG. 1, and is rectangular in the first embodiment. The bottom plate 30 has a length $L_{30}$ that is sufficiently longer than the length $L_1$ of the central plate 11 and is about equal to the length $L_1$ of the central plate 11 plus the combined widths $W_2$ and $W_4$ of the cathode and anode buffer reservoirs 40, 50 to support the top plate assembly 10. The bottom plate 30 has a length $L_{30}$ of from about 40 cm to about 75 cm, a width $W_{30}$ of from about 20 cm to about 30 cm, and a thickness $T_{30}$ from about 5 mm to about 8 mm.

Similar to the central plate 11, the bottom plate 30 is constructed of a suitable material, capable of withstanding the conditions of electrophoresis, such as, but not limited to, glass, alumina ceramic and glass-filled epoxy. In the first embodiment, the bottom plate 30 is constructed of glass. The top surface 30a of the bottom plate 30 is polished to a flatness of about 1 $\mu$m per inch to ensure uniformity with the bottom surface 11b of the central plate 11. When the electrophoresis cassette 100 is used with samples to be read optically, the bottom plate 30 is constructed of glass with low fluorescence characteristics, such as BK7 glass or Borofloat glass. If an ultraviolet photoinitiator is used to polymerize gels, the bottom plate 30 is constructed of BK7 or Borofloat glass, which provides good transparency at wavelengths of about 312 nanometers.

The spacer 20, as shown in FIGS. 1 and 2, has a continuous frame-type configuration with a substantially uniform surface that is mounted to the top surface 30a of the bottom plate 30. The spacer 20 is engaged with the bottom plate 30 substantially adjacent to an outer perimeter of the bottom plate 30. The spacer is from about 8 mm to about 12 mm wide, and a thickness of from about 50 µm to about 200 µm. When assembled in the electrophoresis cassette 100 between the bottom plate 30 and the central plate 11, the spacer 20 defines the thickness of electrophoretic gels. The thickness of the spacer 20 is, therefore, selected according to the application in which the electrophoresis cassette 100 will be used to help optimize the electrophoresis results. For example, if the electrophoresis cassette 100 were used for DNA sequencing, the thickness of the spacer would be less than 100 µm. The spacer 20 is constructed of a suitable material capable of withstanding the conditions of electrophoresis, such as, but not limited to MYLAR® or other film material that provides uniform thickness. Alternatively, the spacer 20 may be of any sufficiently durable material, such as epoxy or silicone rubber, applied permanently to the bottom plate 30 or the top plate assembly 10.

Figure 9:
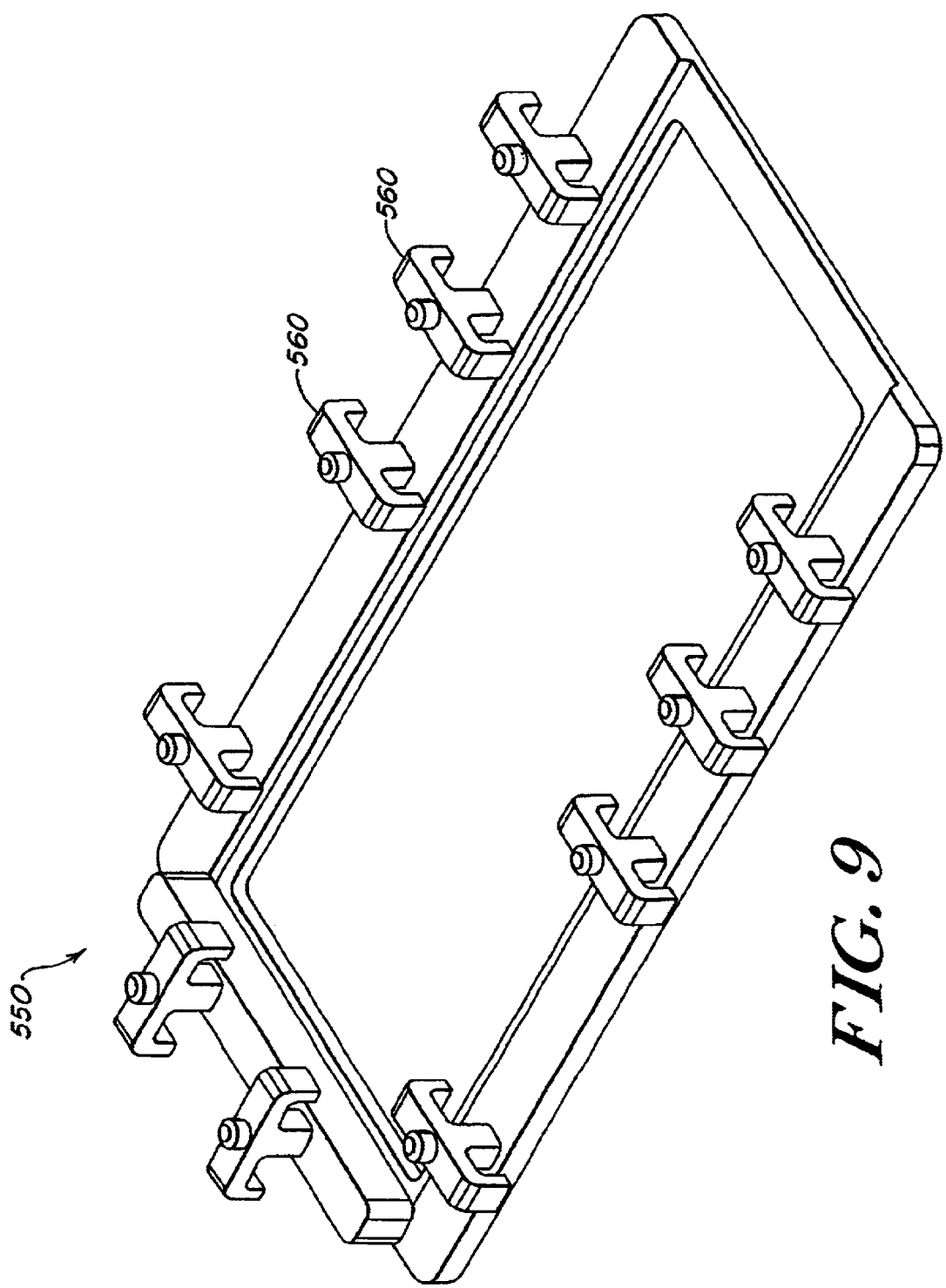
FIG. 9 is a perspective of a clamping/assembly fixture of fifth embodiment.

The electrophoresis cassette 100 of the first embodiment is assembled by mounting the spacer 20 to the top surface 30a of the bottom plate 30, and subsequently mounting the top plate assembly 10 to a top surface 20c of the spacer such that the bottom surface 11b of the central plate 11 rests upon the top surface 20c of the spacer. The assembled components are held in close proximity to one another by clamping mechanisms, such a binder clips, commonly know in the art, or by clamping/assembling fixture as illustrated in FIG. 9 and described herein.

Figure 12:
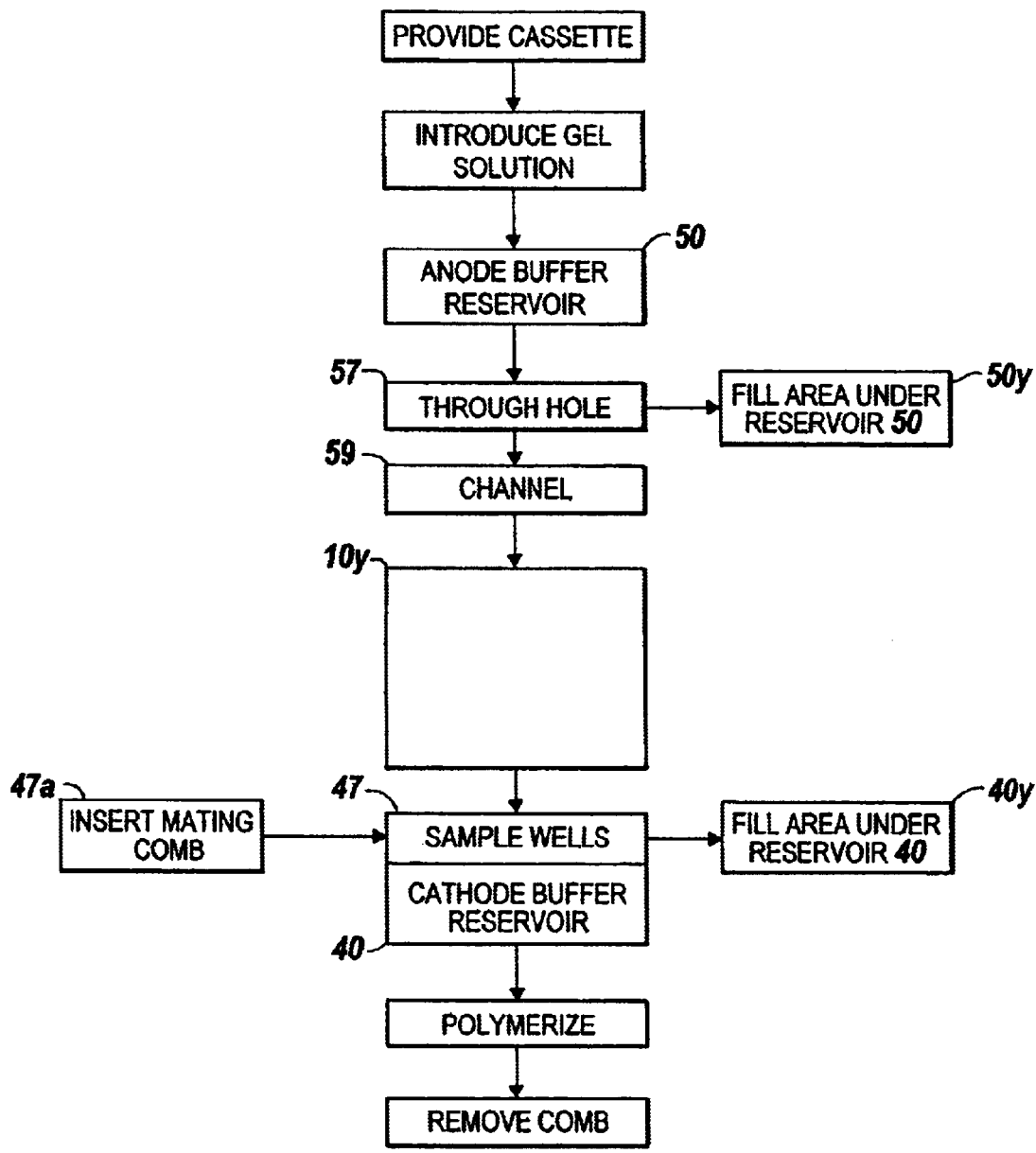
FIG. 12 is a flow diagram illustrating a method of gel casting with the electrophoresis cassette of the first embodiment.

To cast electrophoretic gels, the electrophoresis cassette 100 is assembled as described above. As illustrated in FIG. 12, a gel solution suitable for molding an electrophoretic gel is poured or injected into the anode buffer reservoir 50. The gel solution may include a solution of agarose or various synthetic polymers well known in the art. Alternatively, the gel solution may include a solution of acrylamide, or modified a acrylamide monomers, a N,N'-methylene-bisacryladmide, or a similar crosslinking agent well known in the art, the a ratio of from about 19:1 to about 29:1 for in situ polymerization of the electrophoretic gel.

The gel solution flows into a substantially fills the through slot 57 of the planar base 58 of the anode buffer reservoir 50. The gel solution then flows into and substantially fills the channel 59 disposed between the through slot 57 and the opening 159 of the side wall 50a. The gel solution flows under the anode buffer reservoir 50 to file an area 50y under the anode buffer reservoir 50 between the top surface 30a of the bottom plate and a bottom surface of the anode buffer reservoir 50.

Although the through slot 57, the channel 59 and the area 50y beneath the anode buffer reservoir 50 are said to be filled, it is understood that these components, as well as other components of the electrophoresis cassette 100, are not perfectly filled to 100% capacity, but are substantially filled with gel solution.

The gel solution flows from the channel 59 of the anode buffer reservoir 50 and continues to flow between the bottom surface 11b of the central plate 11 and the top surface 30a of the bottom plate 30, substantially filling a molding space 10y defined by the central plate 11, the spacer 20 and the bottom plate 30. The gel solution substantially fills the molding space 10y and finally flows into and substantially fills the plurality of sample loading wells 47 mounted flush with the cathode edge 11c of the cathode buffer reservoir 40. The gel solution similarly flows under the cathode buffer reservoir 40 to fill an area 40y beneath the cathode buffer reservoir 40 between the top surface 30a of the bottom plate 30 and a bottom surface of the cathode buffer reservoir 40.

The mating comb 47a is inserted in the plurality of sample loading wells 47 and displaces the gel solution from individual sample loading wells. The mating comb 47a remains inserted in the plurality of sample loading wells 47 until the gel solution polymerizes. When the gel solution is polymerized, the mating comb 47a is removed from the plurality of sample loading wells 47. Individual sample loading wells are free of polymerized gel and ready to receive samples.

Thin layers of polymerized gel seal the plurality of sample loading wells 47 with the top surface 30a of the bottom plate 30 and with the cathode edge 11c of the central plate 11 to form leak-proof seals. In addition, the cathode buffer reservoir 40 is sealed by polymerized gel to the top surface 30a of the bottom plate 30 to form a leak-proof seal. The opening 159, the channel 59 and the through slot 57 of the anode buffer reservoir 50 are sealed with polymerized gel to form a leak-proof seal with the anode buffer reservoir 50. Polymerized gel in the area 50y beneath the anode buffer reservoir 50 forms a leak-proof seal with the top surface 30a of the bottom plate 30 and a bottom surface of the anode buffer reservoir 50.

Electrophoresis of samples in the polymerized gel proceeds as described below. The cathode buffer reservoir 40 and the plurality of sample loading wells 47 are filled with distilled water or a dilute salt solution to serve as a sample injection solution. The anode buffer reservoir 50 is concurrently filled with electrolytic buffer solution. Samples are dispensed into the plurality of sample loading wells 47 either manually or with automatic dispensing equipment. The samples are injected into the electrophoretic gel by a brief pulse of high voltage, for example 5000 V for 30 seconds, applied to the cathode buffer reservoir 30. The sample injection solution is removed from the cathode buffer reservoir 40 which is subsequently filled with a concentrated electrolytic buffer solution of an appropriate concentration. Electrical current is then supplied to the electrophoresis cassette 100 for electrophoresis to proceed.

The electrophoresis cassette 100 is used in connection with an external electrical power supply which provides electrical current required for sample injection and electrophoresis. The electrical power supply is detachably connected to the electrophoresis cassette 100 by means of the cathode connector 46 provide electrical current to the cathode buffer reservoir 40, and by means of the anode connector 56 to provide electrical current to the anode buffer reservoir 50. The electrical power supply is capable of supplying the proper voltage and current required for various electropharesis applications. For example, with respect to analysis of DNA fragments, the voltage and current required for electrophoretic separation of DNA fragments is about 5000 volts and 40 mA.

The electrophoresis cassette 100 is used in conjunction with a temperature control mechanism to maintain temperature of the electrophoretic gel within the acceptable range required of the particular application. For example, in low-power applications, temperature may be maintained by radiative and convective cooling to ambient air. In high power applications, temperature may be actively controlled by use of such temperature control mechanisms as turbulent forced air, air-cooled or water-cooled jacket assemblies, or temperature controlled water.

The electrophoresis cassette 100 is used with a variety of methods that are well known in the art for detection of molecular components in gels. For example, the electrophoresis cassette 100 may be used with numerous techniques for detection of DNA molecules, such as, but not limited to, use of fluorescent tags for induced fluorescence, ethidium bromide staining, autoradiography, or Southern blotting. The electrophoresis cassette 100 may also used be used with techniques for detection of proteins, such as, but not limited to, autoradiography, Western blotting or staining with Coomassie Blue or silver.

Figure 5:
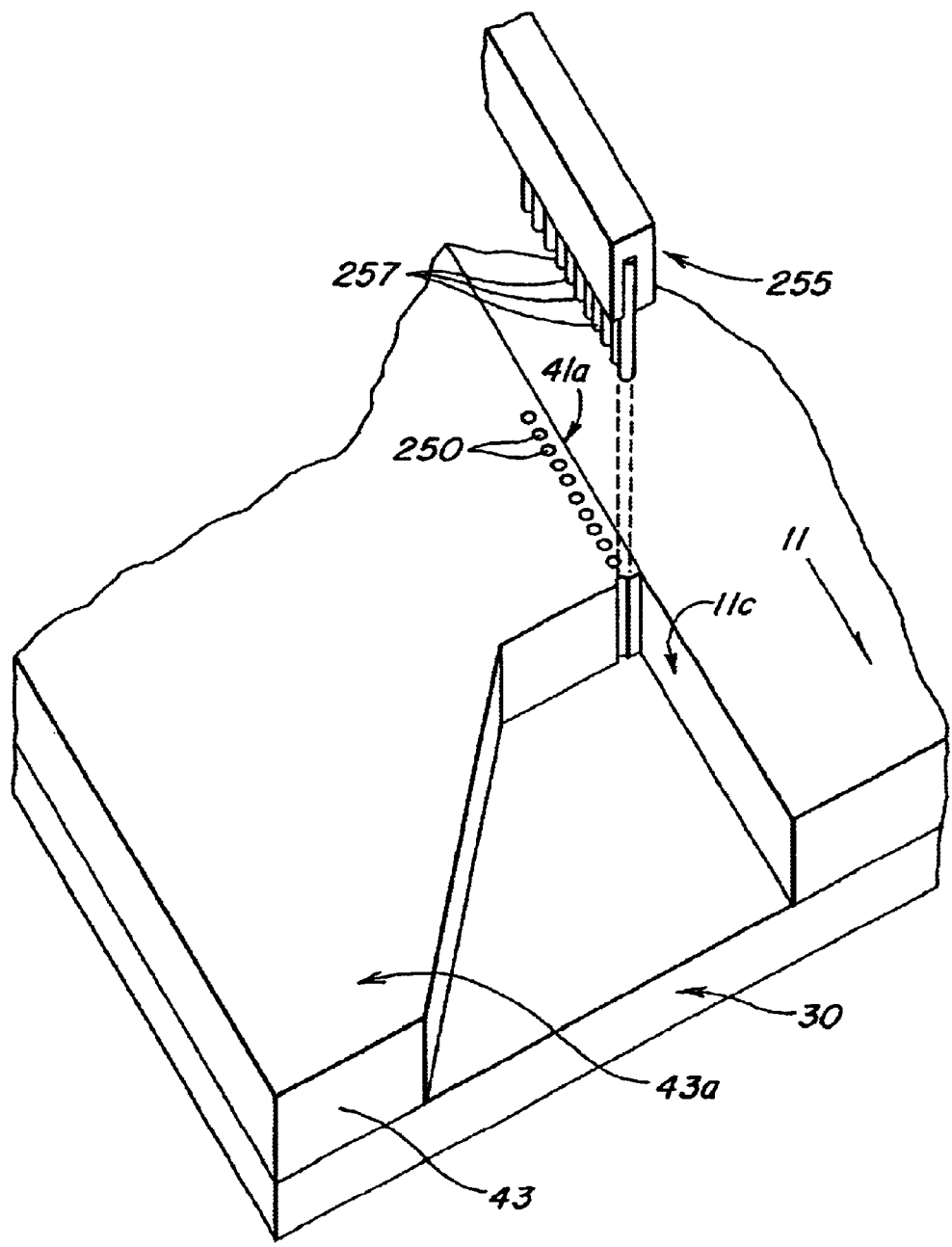
FIG. 5 is a cross-sectional perspective of a plurality of sample loading wells of a second embodiment.

Referring to FIG. 5, a second embodiment of the invention comprises an electrophoresis cassette of identical construction to the electrophoresis cassette 100 of the first embodiment with the exception that sample loading wells are formed by machining or molding a plurality of through holes 250 in the bottom surface 43a of the cathode reservoir base 43. The plurality of sample loading wells 250 is arranged in a linear array and positioned adjacent to the first side wall 41a of the cathode reservoir base 43. As shown in FIG. 5, the sample loading wells are circular cylinders, although the invention is not limited to sample loading wells of any particular shape. Circular cylindrical sample loading wells are used in the present embodiment to facilitate ease in manufacture.

A mating comb 255 is provided in the second embodiment including a plurality of teeth or prongs of similar number and configuration as the plurality of sample loading wells 250. As in the first embodiment, the mating comb 255 is used to effectively displace gel solution during gel casting to prevent polymerization of gel solution in sample loading wells.

In the second embodiment, the first side wall 41a of the cathode reservoir base 43 is free of sample loading wells. Such structure and construction permits epoxy adhesive to be applied along the entire length $L_2$ of the cathode reservoir base 43 to adhesively join the cathode reservoir base 43 to the cathode edge 11c of the central plate 11 to form a leak-proof seal.

Figure 6:
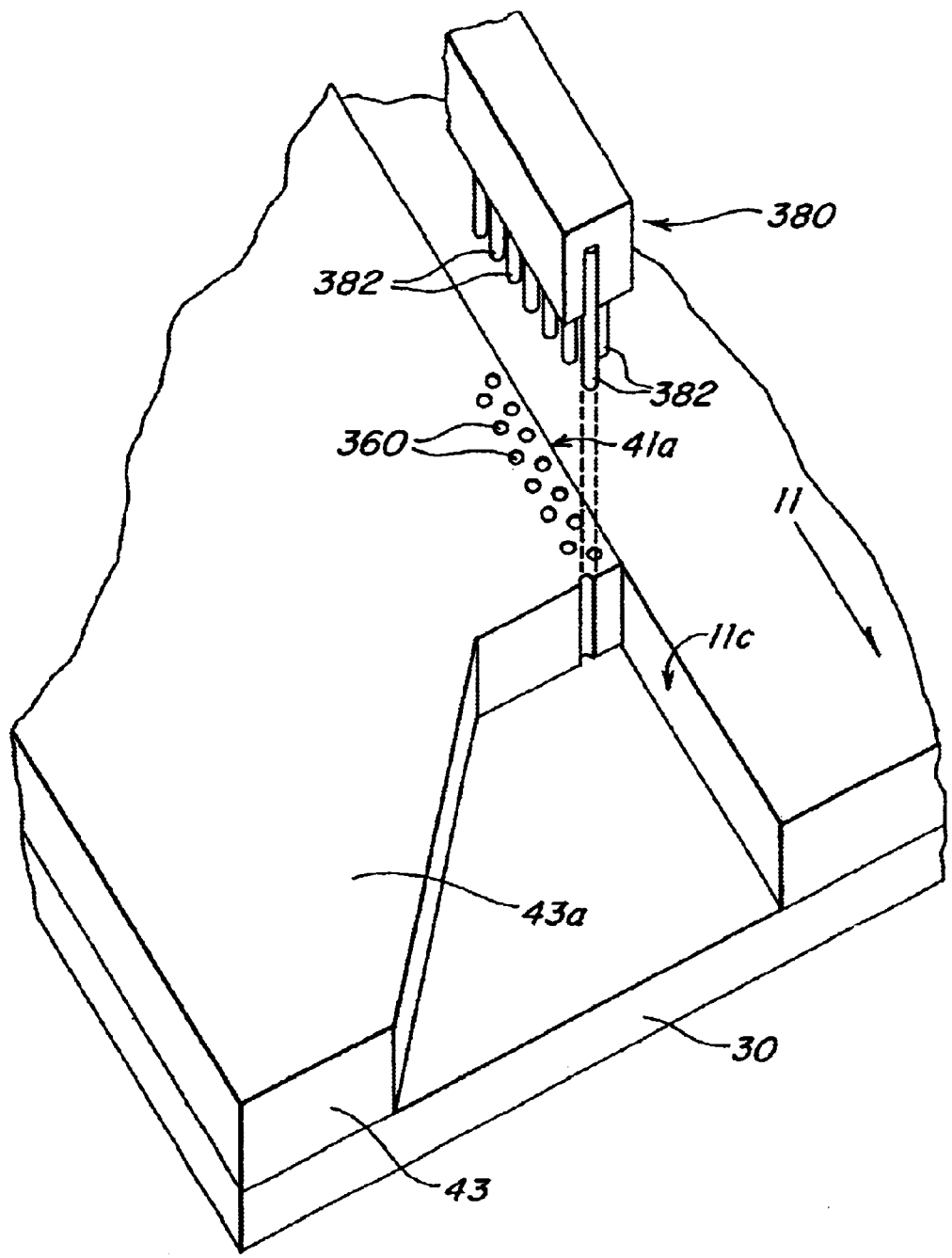
FIG. 6 is a cross-sectional perspective of a plurality of sample loading wells of a third embodiment.

A third embodiment of the invention comprises an electrophoresis cassette of identical construction to the electrophoresis cassette 100 of the first embodiment with the exception that sample loading wells are formed by machining or molding a plurality of through holes 360 in the bottom surface 43a of the cathode reservoir base 43, as illustrated in FIG. 6. The plurality of sample loading wells 360 is arranged in multiple, for instance dual, parallel linear arrays. Individual wells of each linear array are physically staggered in relation to individual wells of the other array. Such staggered parallel arrays of sample loading wells facilitate staggered sample loading. Staggered sample loading is a technique used to identify sample lanes formed in gels as samples migrate through electrophoretic gels. Typically, such a "lane tracking" technique is performed by temporally staggering the loading and electrophoretic injection of samples into an electrophoretic gel. A first set of samples is loaded and injected into a gel during a first injection cycle arid a second set of samples is loaded and injected during a second injection cycle after a lapse of a predetermined period of time. Temporally staggering sample loading and injecting usually requires the assistance of an operator and is not conducive to automated dispensing equipment. The plurality of staggered sample loading wells 360 of the third embodiment spatially staggers injection of samples into electrophoretic gels to permit sample lane identification. The staggered plurality of sample loading wells 360 permits the use of automated dispensing equipment and requires only a single sample injection cycle.

As in the second embodiment, sample loading wells are circular cylinders to facilitate manufacturing. In addition, a mating comb 380 is similarly provided that includes a plurality of teeth or prongs 382 similar in number and configuration as the plurality of sample loading wells 360.

As in the second embodiment, the cathode reservoir base 43 receives an application of epoxy adhesive along its entire length $L_2$ to adhesively join the cathode reservoir base to the cathode edge 11c of the central plate 11 to form a leak-proof seal.

Figure 7A:
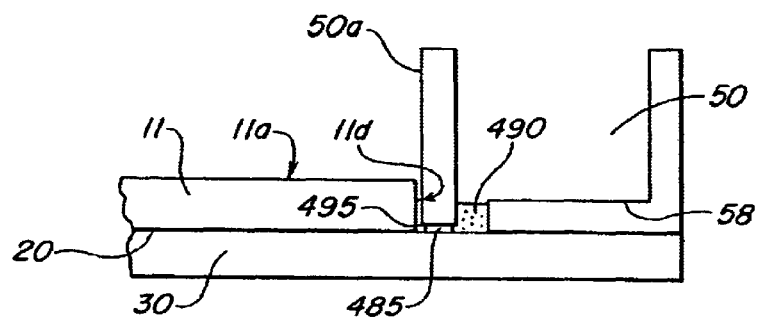
FIG. 7a is a cross-sectional side view of the anode buffer reservoir incorporated with the electrophoresis cassette of the fourth embodiment.
Figure 7:
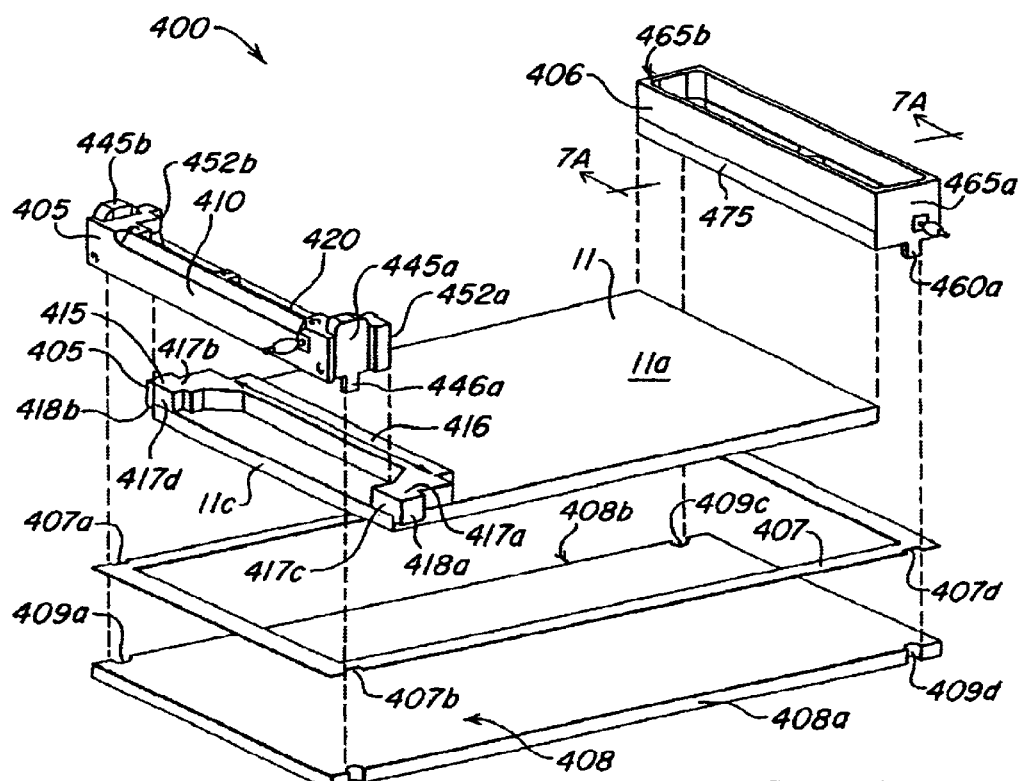
FIG. 7 is a exploded perspective of an electrophoresis cassette of a fourth embodiment.
Figure 8:
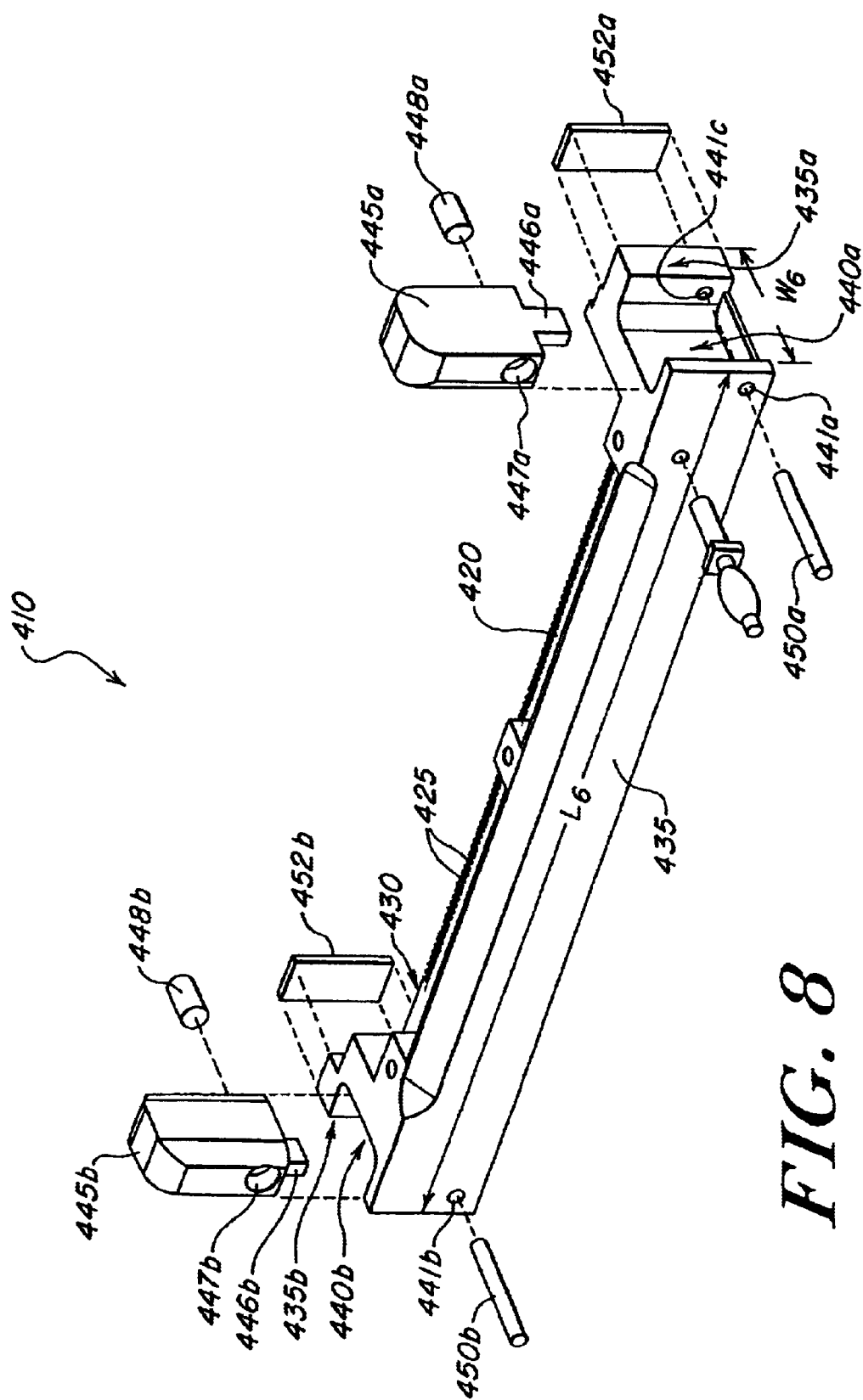
FIG. 8 is an exploded perspective of a cathode reservoir body with biasing slide blocks.

A fourth embodiment of the invention is illustrated in FIGS. 7, 7a and 8 and provides an electrophoresis cassette 400 similar to the electrophoresis cassette 100 of the first embodiment with the exception that a cathode buffer reservoir 405, an anode buffer reservoir 406, and the central plate 11 are not permanently joined into a single assembly, but rather, are held together as an assembly during gel casting and electrophoresis by means of a mechanical biasing system.

FIG. 7 illustrates the fourth embodiment which includes the cathode buffer reservoir 405, the anode buffer reservoir 406, the central plate 11, a spacer 407 and a bottom plate 408. The cathode buffer reservoir 405 comprises a cathode reservoir body 410, a pair of slide blocks 445a, 445b, and a proximal cathode perimeter wall 415.

Referring also to FIG. 8, the cathode reservoir body 410 includes a bottom planar base 420 with a plurality of sample loading wells 425 incorporated with an inner side wall 430 of the bottom base 420. The plurality of sample loading wells 425 is positioned flush with the cathode end 11c of the central plate 11 when the cathode buffer reservoir is assembled and joined with the central plate 11.

The cathode reservoir body 410 includes elements which comprise a mechanical biasing system that biases the central plate 11 against the cathode buffer reservoir 405 to help assembly of the electrophoresis cassette 400. As shown in FIG. 8, the cathode reservoir body 410 includes an outer side wall 435 with a length $L_6$ of from about 20 cm to about 30 cm, and a width $W_6$ of from about 4 cm to about 8 cm. Ends of the cathode reservoir body 410 provide recesses 440a, 440b that receive the slide blocks 445a, 445b. The recesses 440a, 440b of the fourth embodiment have a U-shaped configuration to accommodate the slide blocks 445a, 445b, but may be configured in other geometries to receive slide blocks of different dimensions. The slide blocks 445a, 445b include locating pins 446a, 446b which protrude downwardly from bottom portions of the slide blocks 445a, 445b and facilitate positioning of the cathode reservoir body 410 relative to the bottom plate 408. The slide blocks 445a, 445b and locating pins 446a, 446b are constructed of a durable material with a high dielectric constant, such as, but not limited to, a high molecular weight polymer, including DELRIN® available from DuPont of Wilmington, Del.

Mounting rods 450a, 450b secure the slide blocks 445a, 445b in each recess 440a, 440b. As shown in FIG. 8, a portion of each U-shaped recess 440a, 440b includes a first and a second through hole 441a, 441b and 441c, 441d that slidably receive the mounting rods 450a, 450b. Bores 447a, 447b located in side portions of the slide blocks 445a, 445b also slidably receive the mounting rods 450a, 450b. To mount the slide blocks 445a, 445b, the mounting rods penetrate the first through holes 441a, 441b, and pass through the bores 447a, 447b, and are finally received by the second through holes 441c, 441d (not shown). The slide blocks 445a, 445b are mounted in the recesses 440a, 440b such that the mounting rods limit upward and downward vertical movement of the slide blocks. However, diameters of the bores 447a, 447b are sufficiently wide to permit the slide blocks to move longitudinally forward and backward along the mounting rods 450a, 450b in parallel relation to the length $L_1$ of the central plate 11. Prior to being received by the second through holes 441c, 441d, the mounting rods 450a, 450b are slidably received by springs 448a, 448b, which are slidably received by the bores 447a, 447b of the locating slide blocks 445a, 445b. Biasing tension to hold and maintain cassette components in proximity with one another is provided by compression of the biasing springs as the slide blocks 445a, 445b move longitudinally backward in a direction away from and parallel to the central plate 11 and the anode buffer reservoir 406.

The proximal cathode perimeter wall 415 is adhesively mounted to the top surface 11a of the central plate 11, as shown in FIG. 7, and constructed in a U-stapled configuration, including a side wall 416 and a first and second end portion 417a, 417b. Suitable materials capable of withstanding the conditions of electrophoresis, such as, but not limited to, acrylic are used to construct the proximal cathode perimeter wall 415. The side wall 416 of the proximal cathode perimeter wall 415 has a length $L_7$ of at least as long as the width $W_1$ of the central plate 11. The proximal cathode perimeter wall 415 is substantially flat and uniform with a thickness of from about 1 cm to about 3 cm, and in the present embodiment about 1 cm thick.

The proximal cathode perimeter wall 415 is adhered to the top surface 11a of the central plate 11 by GE Silicone RTV Adhesive available from GE Silicones of Waterford, N.Y., or Extreme-Katiobond 1052 available from Extreme Adhesives of Seabrook, N.H.

The first and second end portions 417a, 417b of the cathode reservoir perimeter 415 terminate at the cathode edge 11c of the central plate 11. Terminal end surfaces 417c, 417d of the first and second end portions 417a, 417b are substantially even with the cathode edge 11c. Reference point protrusions 418a, 418b extend laterally at a terminal section of the first and second end portions 417a, 417b to ensure that the first and second end portions are in consistent alignment with the cathode end 11c of the central plate 11.

As shown in FIG. 7, the anode buffer reservoir 406 is substantially similar in construction to the anode buffer reservoir 50 of the first embodiment except that the anode buffer reservoir includes permanent locating pins 460a, 460b (only 460a shown in FIG. 7) that extend downwardly from a lower section of a first and second end portion 465a, 465b of the anode buffer reservoir 50. The permanent locating pins 460a, 460b facilitate positioning of the anode buffer reservoir relative to the bottom plate 408.

Referring to FIG. 7a, a channel 485 is defined in a lower section of the side wall 50a of the anode buffer reservoir 406 by the bottom plate 30 and between a through slot 490 positioned off-center in the planar base 58 and an opening 495 in the side wall 50a. The channel 485 is in fluid communication with the opening 495, as shown in FIG. 7a. The opening 495 is raised upward from a bottom of the first side wall 50a more than a thickness of an electrophoretic gel contained in the electrophoresis cassette 400 and less than the height of the central plate 11. FIG. 7a illustrates a cross-sectional side view of the anode buffer reservoir 406 when assembled with the central plate 11 and the bottom plate 30. The channel 59 is positioned between the anode edge 11d of the central plate 11 and the through slot 490.

Since the anode buffer reservoir 406 of the fourth embodiment is not permanently attached to the central plate 11, a seal between the anode buffer reservoir 406 and the anode edge 11d of the central plate 11m is achieved by a gasket 475 and polymerized gel. When gel casting is complete, an area under the anode buffer chamber 406 between the top surface 30a of the bottom plate 30 and a bottom surface of the anode buffer chamber 406 is filled with polymerized gel to create a leak-proof seal between the anode buffer reservoir 406 and the central plate 11 and the bottom plate 30.

The spacer 407 and the bottom plate 408 are substantially similar in construction to the spacer 20 and the bottom plate 30 of the first embodiment except that they are constructed with features to facilitate positioning and attachment of the cathode buffer reservoir 405 and the anode buffer reservoir 406 to the bottom plate 408. As shown in FIG. 7, the bottom plate 408 contains slots 409a, 409b, 409c, 409d approximately 1.5 cm from each corner along first and second sides 408a, 408b to receive the locating pins 446a, 446b of the cathode reservoir buffer 405 and the permanent locating pins 460a, 460b of the anode buffer reservoir, respectively. Similarly, the spacer 407, to facilitate positioning and attachment of the cathode and anode buffer reservoirs 405, 406, includes notches 407a, 407b, 407c, 407d at approximately each corner to receive the locating pins 446a, 446b of the cathode reservoir buffer 405 and the permanent locating pins 460a, 460b of the anode reservoir buffer 406.

The electrophoresis cassette 400 of the fourth embodiment is assembled by placing a bottom surface of the spacer 407 on a top surface of the bottom plate 408, and placing the cathode reservoir body 410 in contact with an upper surface of the spacer 20. The locating pins 446a, 446b of the cathode reservoir body 410 are inserted through the notches 407a, 407b of the spacer and into the slots 409a, 409b of the bottom plate 408 to securely connect the cathode reservoir body 410 to bottom plate 408. The central plate 11, with the cathode reservoir perimeter 415 adhesively mounted to the top surface 11a, is placed upon the upper surface of the spacer 407.

The cathode edge 11c of the central plate 11 is positioned flush with the plurality of sample loading wells 425, while the terminal end surfaces 417c, 417d of the cathode reservoir perimeter 415 are each flush with one of a pair of gaskets 452a, 452b of the cathode reservoir body 410. The central plate 11 is manually forced against the cathode reservoir body 410 which compresses the biasing springs 448a, 448b of the locating slide blocks 445a, 445b. Such compression of the biasing springs 448a, 448b helps the cathode edge 11c and the terminal end surfaces 417c, 417d to make firm contact with the cathode reservoir body 410.

While the central plate 11 is in this position, the anode buffer reservoir 406 is similarly mounted to the central plate 11 by inserting the permanent locating pins 460a, 460b through the notches 407c, 407d of the spacer and into the slots 409c, 409d of the bottom plate to securely connect the anode buffer reservoir to the bottom plate and position the anode buffer reservoir flush with the anode edge 11d of the central plate 11. Once the anode buffer reservoir 406 has been secured to the bottom plate 408, the central plate 11 is manually released whereupon the biasing springs 448a, 448b expand and the central plate 11 is compressed between the cathode buffer reservoir 405 and the anode buffer reservoir 406. The cathode and anode reservoir buffers 405, 406 are held firmly flush against the cathode end 11c and the anode end 11d of the central plate 11 with a sufficient pressure to facilitate formation of leak-proof seals between the buffer reservoirs 405, 406 and the cathode and anode edges 11c, 11d of the central plate 11. In addition, the pressure with which the central plate 11 and bottom plate are held together is sufficient to prevent leakage of buffer fluid from the electrophoresis cassette 400 when assembled.

Gel casting is accomplished in accordance with the method of the first embodiment. In addition, sample injection and electrophoresis subsequently proceed as described in the first embodiment.

A fifth embodiment of the invention is illustrated in FIG. 9 and includes a clamping/assembling fixture 550 suitable for use in assembling any of thee electrophoresis cassettes described in the previous embodiments. The clamping/assembling fixture 550 has a frame-type configuration with a length and a width slightly larger than similar dimensions of the electrophoresis cassettes to be assembled therein. The clamping/assembling fixture 550 includes a plurality of fasteners 560 disposed along at least three sides of the fixture 550 to hold, as in the case of the first, second and third embodiments, the central plate 11, the spacer 20 and the bottom plate 30 in correct alignment and in close proximity during gel casting. The plurality of fasteners 560 may include screw-type or spring-biased clamps that pressure the central plate 11 against the spacer 20 and the bottom plate 30 when secured.

Referring to FIG. 6, a sixth embodiment of the invention include an electrophoresis cassette 600 similar to the electrophoresis cassette 100 of the first, second and third embodiments except that the cassette 600 includes mechanical biasing mechanisms, a cathode blank 640 and a modified spacer 650.

Figure 10:
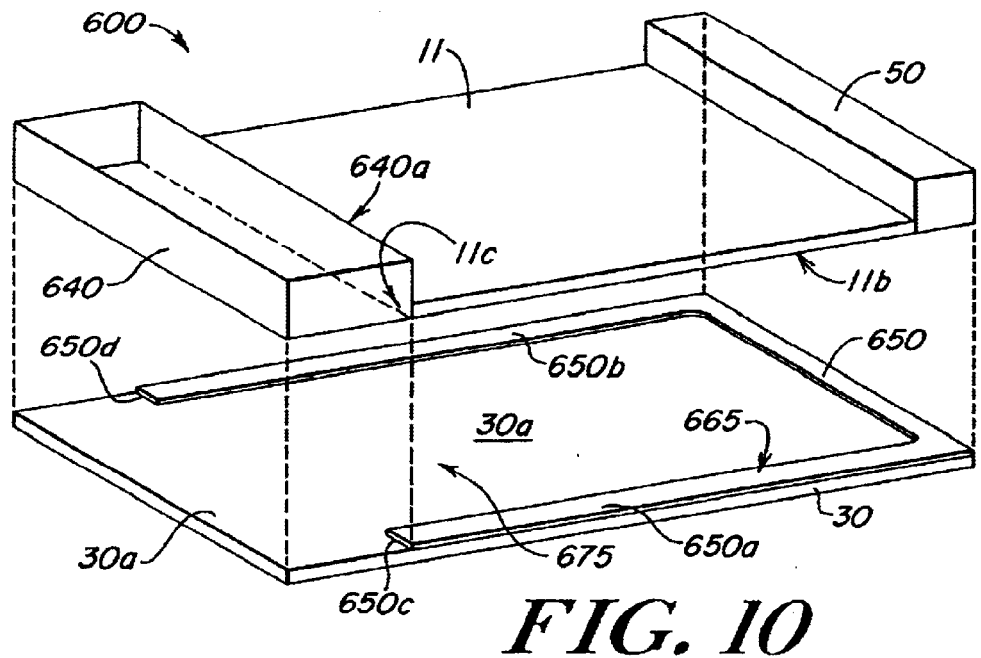
FIG. 10 is an exploded perspective of an electrophoresis cassette of sixth embodiment.

The electrophoresis cassette 600 of the sixth embodiment is illustrated in FIG. 10 and includes the modified spacer 650 constructed of a suitable material, such as MYLAR®, and having a U-shaped frame. The modified spacer 650 is about 1 cm wide and has a thickness of about 50 μm. When engaged with the top surface 30a of the bottom plate 30, the modified spacer 650 is contiguous in an area under the anode buffer reservoir 50 with a first side arm 650a and a second side arm 650b opening toward the cathode buffer reservoir 40. The first and second side arms 650a, 650b of the modified spacer 650 terminate on the bottom plate 30 at a location that positions a first terminal edge 650c of the first side arm 650a and a second terminal edge 650d of the second side arm 650b in flush alignment with the cathode edge 11c when the central plate 11 is engaged with an upper surface 665 of the modified spacer 650.

The solid cathode blank 640 has a substantially identical length and width as the length $L_2$ and the width $W_2$ of the cathode reservoir base 43 of the cathode buffer reservoir 40 of the first embodiment. When the cathode block 640 is engaged with the top surface 30a of the bottom plate 30 and flush with the cathode edge 11c, the cathode block 640 substantially covers or blanks out an area occupied by the cathode buffer reservoir 40 when the electrophoresis cassette 600 is assembled.

The cathode blank 640 is used during gel casting to replace the cathode buffer reservoir 40 and to serve as a template to restrict flow of gel solution. The cathode blank 640 does not include sample loading wells and, therefore, is flush with the cathode edge 11c of the central plate 11 when engaged with the bottom plate 30 and the central plate 11. As shown in FIG. 10, a side wall 640a of the cathode blank which extends the width $W_1$ of the central plate 11 is flush with the cathode edge 11c of the central plate 11 and the first and second terminal edges 650c, 650d of the modified spacer.

The cathode buffer reservoir 40, the anode buffer reservoir 50, the central plate 11, the modified spacer 640 and the bottom plate 30 of the sixth embodiment are joined and held together by any mechanical biasing mechanisms such those disclosed in U.S. Pat. Nos. 5,242,568, 5,228,971, and 5,137,613, incorporate herein by reference, to form the electrophoresis cassette 600.

Figure 13:
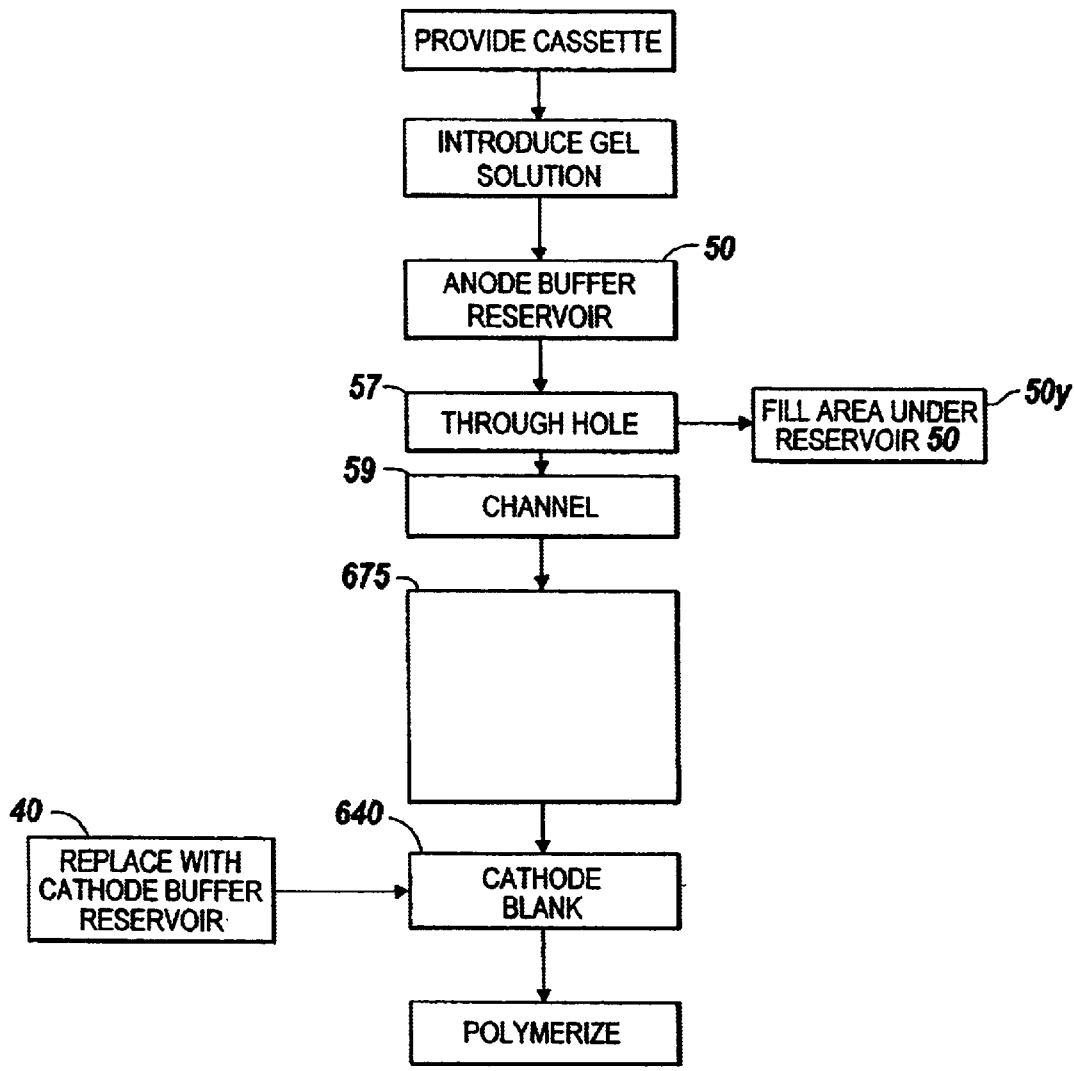
FIG. 13 is a flow diagram illustrating a method of gel casting with the electrophoresis cassette of the sixth embodiment.

A biasing mechanism for biasing the cathode buffer reservoir toward the cathode edge 11c of the central plate 11 when the cathode reservoir is engaged with the central and bottom plates includes a cam mechanism as disclosed in U.S. Pat. No. 5,242,568 (col. 7, lines 64–68–col. 8, lines 1–16; FIGS. 13 and 19), incorporated herein by reference. When the cam mechanism is engaged, the cathode reservoir base 43 is biased toward tile cathode edge 11c of the central plate 11 such that the plurality of sample loading wells 47 that are incorporated with the first side wall 41a of the cathode reservoir base 43, is flush with the cathode edge 11c of the central plate 11. The plurality of sample loading wells 47 is held against the cathode edge 11c with sufficient force so as to form a uniform interface between the cathode edge 11c and an edge of the polymerized gel previously molded therein. The uniform interface prevents leakage of buffer solution and facilitates consistent injection of samples into gels.

Figure 14:
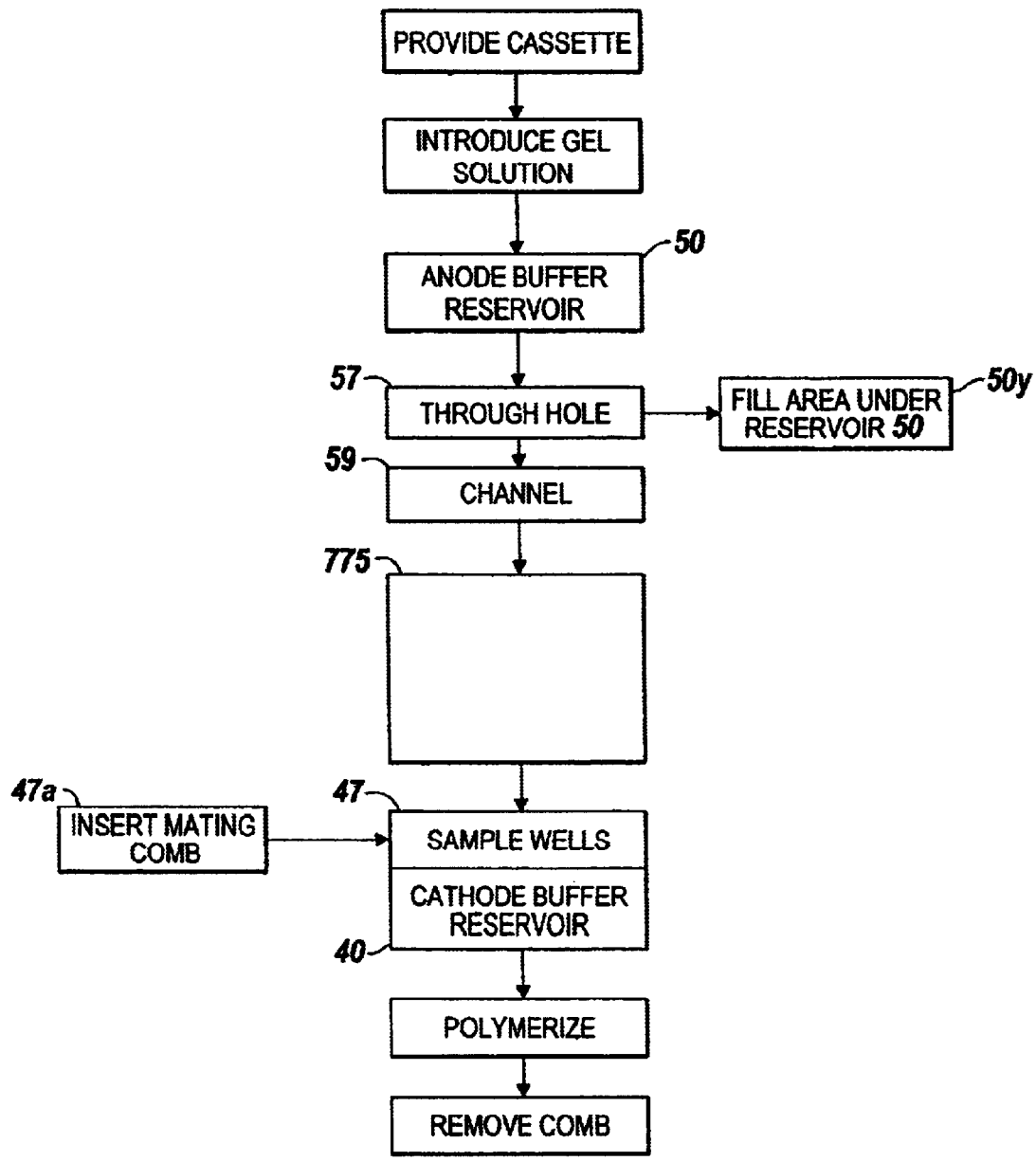
FIG. 14 is a flow diagram illustrating a method of gel casting with the electrophoresis cassette of the seventh embodiment.

Similarly, a biasing mechanism for biasing the anode buffer reservoir 50 toward the anode edge 11d of the central plate 11 when the anode reservoir is engaged with the central and bottom plates 11, 30, includes a cam mechanism as disclosed in U.S. Pat. No. 5,242,568 (col. 8. Lines 30–64; FIGS. 14 and 39), incorporated herein by reference. The cam mechanism biases the anode buffer reservoir 50 toward the anode edge 11d of the central plate 11 such that the first side wall 50a of the anode buffer reservoir is flush with the anode edge 11d to form a uniform interface of the anode edge 11d and the first side wall of the anode buffer reservoir 50.

Biasing mechanisms are also provided for biasing the top plate assembly 10, including the cathode and anode buffer reservoirs 40, 50 and the central plate 11, downwardly against the upper surface 665 of the modified spacer 650 and the top surface 30a of the bottom plate 30, as disclosed in U.S. Pat. No. 5,242,568 (col. 9, lines 29–68–col. 10, 1–21; FIGS. 16 and 25), incorporated herein by reference. The biasing mechanisms include at least one biasing mechanism that biases the cathode buffer reservoir 40 downwardly toward the central plate 11 and the bottom plate 30, at least one biasing mechanism that biases the anode buffer reservoir 50 downwardly toward the central plate 11 and the bottom plate 30, and a plurality of biasing mechanisms that bias side portions of the central plate 11 downwardly toward the central plate 11 and the bottom plate 30.

To cast electrophoretic gels according to the sixth embodiment of the invention, the electrophoresis cassette 600 is assembled and biased as described above. As illustrated in FIG. 13, a gel solution suitable for molding an electrophoretic gel is poured or injected into the anode buffer reservoir 50 and gel casting proceeds in accordance with the method of the first embodiment with the exception that the cathode blank 640 is inserted at the cathode edge 11c of the central plate 11. The cathode blank 640 acts as a template and restricts flow of the gel solution during casting to help prevent flow of gel solution beyond the first and second terminal edges 650c, 650d of the modified spacer 650.

The gel solution flows between the bottom surface 11b of the central plate 11 and the top surface 30a of the bottom plate 30, substantially filling a molding space 675 defined by the central plate 11, the modified spacer 650, and the bottom plate 30. The gel solution flows toward the cathode blank 640 and is prevented from flowing beyond the first and second terminal edges 650c, 650d of the modified spacer 650. After polymerization, the cathode blank 640 is removed. The gel formed between the first and second side arms 650a, 650b is in flush alignment with the cathode edge 11c of the central plate 11. The cathode blank 640 is subsequently replaced by the cathode buffer reservoir 40 of the first embodiment to conduct electrophoresis.

Figure 11:
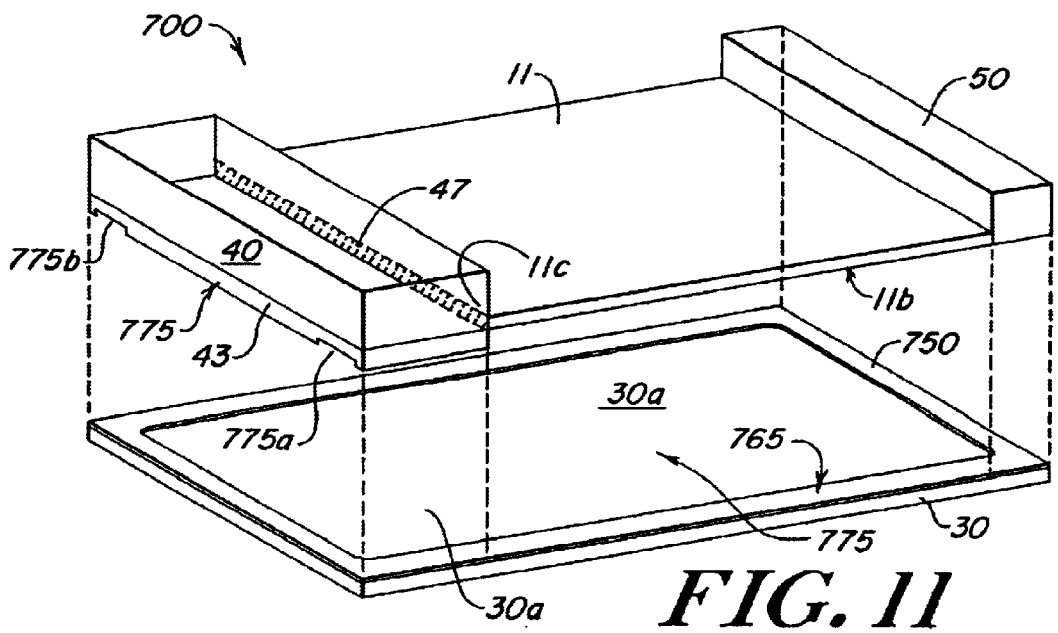
FIG. 11 is an exploded perspective of an electrophoresis cassette of seventh embodiment.

Referring to FIG. 11, a seventh embodiment of the invention includes an electrophoresis cassette 700 similar to the electrophoresis cassette 600 of the sixth embodiment except that the cathode blank 640 and the modified spacer 650 are not used during gel casting, but rather, the cathode buffer reservoir 40 is in place during gel casting. The cathode buffer reservoir 40 is constructed of G10 glass-filled epoxy to form a plurality of "hard well" sample loading wells 47, such as described in the first embodiment.

A spacer 750 with a continuous frame-type configuration, similar to the spacer 20 disclosed in the first embodiment, engages the top surface 30a of the bottom plate 30. The spacer 750 is constructed of MYLAR® and has a width of about 1 cm and a thickness of about 70 μm. The cathode buffer reservoir 40 is engaged with the central plate 11 and the bottom plate 30 and mounted upon and engaged with an upper surface 765 of the spacer 750. The cathode buffer reservoir 40 is not engaged with the top surface 30a of the bottom plate 30, but rather, is raised upward from the top surface 30a of the bottom plate 30 at a distance equal to the thickness of the spacer 750, or about 1 cm. In an alternative embodiment, the U-shaped spacer 650 of the sixth embodiment may be used rather than the continuous spacer 750.

Whether the continuous spacer 750 or the modified U-shaped spacer 650 is employed with the electrophoresis cassette 700, in either alternative the cathode buffer reservoir 40 includes recesses 775a, 775b in a bottom surface 775 of the cathode reservoir base 43. Recesses 775a, 775b have a width and a depth approximately equal to a width and a depth of the spacer 750,650 to allow the recesses 775, 775b to receive: portions of the spacer 750, 650 when the cathode reservoir base 43 is seated to the top surface 30a of the bottom plate 30. The recesses 775a, 775b help to facilitate seating of the cathode buffer reservoir 40 on the top surface 30a of the bottom plate 30.

To cast gels according to the seventh embodiment of the invention, the electrophoresis cassette 700 is assembled as described above and biased as provided in the sixth embodiment. A gel solution suitable for molding an electrophoretic gel is poured or injected into the anode buffer reservoir 50 in accordance with the method according of the first embodiment, as shown in FIG. 14. The gel solution flows into the electrophoresis cassette 700 between the bottom surface 11b of the central plate 11 and the top surface 30a of the bottom plate 30, substantially filling a molding space 775 defined by the central plate 11, the continuous spacer 750, and the bottom plate 30. The gel solution substantially fills the molding area 775. The gel solution finally flows into and substantially fills the plurality of "hard well" sample loading wells 47 positioned flush with the cathode, edge 11c of the cathode buffer reservoir 40.

As in the first embodiment, the mating comb 47a is inserted in the plurality of sample loading wells 47 and displaces the gel solution from individual sample loading wells. The mating comb 47a remains inserted in the plurality of sample loading wells 47 until the gel solution polymerizes. After polymerization, the mating comb 47a is removed from the plurality of sample loading wells 47. Individual sample loading wells are free of polymerized gel and ready to receive samples.

Thin layers of polymerized gel seal the plurality of sample loading wells 47 with the top surface 30a of the bottom plate 30 and with the cathode edge 11c of the central plate 11 to form leak-proof seals. As the cathode buffer reservoir 40 is seated on the top surface 30a of the bottom plate 30, the gel solution is substantially prohibited from flowing under the cathode buffer reservoir 40 between the top surface 30a of the bottom plate 30 and the cathode buffer reservoir 40. However, extremely small amounts of the gel solution permeate under the cathode buffer reservoir 40 to form a seal of polymerized gel between the cathode buffer reservoir 40 and the bottom plate 30. Sample injection and electrophoresis subsequently proceed as described in the first embodiment.

Having thus described at least one illustrative embodiment of the invention, various alterations, modifications and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto.

What is claimed is:

1. An apparatus, for use in casting an electrophoretic gel and performing electrophoresis, comprising:
    a bottom plate;
    a spacer seated on a top surface of the bottom plate;
    a top plate assembly seated on a top surface of the spacer and the top surface of the bottom plate to define a molding space;
    the top plate assembly including:
        a central plate having a length shorter than a length of the bottom plate;
        a first reservoir having a substantially planar base and a body extending from the base to provide a first receptacle for containing fluid, the base being connected to the central plate forming an array bottom;
        the array bottom defining a plurality of sample wells, the wells provide fluid communication between the first receptacle and the molding space;
        a first electrode coupled within the first receptacle; and
        a second reservoir providing a second receptacle for containing fluid and defining a through slot in a bottom surface of the reservoir, the through slot being in fluid communication with the molding space; and
        a second electrode coupled within the second receptacle.

2. The apparatus of claim 1, wherein the plurality of sample wells is disposed along an edge of the planar of the first reservoir.

3. The apparatus of claim 2, wherein the planar base is adhesively connected flush with a first terminal end of the central plate.

4. The apparatus of claim 1, wherein boundaries of the plurality of sample wells are constructed of rigid, electrically non-conductive material.

5. The apparatus of claim 1, wherein the plurality of sample wells is a linear array of through holes.

6. The apparatus of claim 1, wherein the plurality of sample wells are multiple linear arrays with individual sample wells of a first linear array positioned in staggered parallel relation to individual sample wells of a second linear array.

7. The apparatus of claim 1, wherein the top plate assembly is configured such that the plurality of sample wells can receive a mating comb including a plurality of teeth, wherein individual teeth have substantially the same geometry and overall dimensions as individual sample wells.

8. The apparatus of claim 1, wherein the second reservoir is adhesively connected flush with a second terminal end of the central plate.

9. The apparatus of claim 1, wherein the bottom plate, the top plate assembly, and the spacer are held together by pressure provided by clamping devices.

10. The apparatus of claim 1, wherein the first reservoir contains a biasing mechanism such that a first terminal end of the central plate is biased against the plurality of sample loading wells.

11. A method of forming an electrophoretic gel, the method comprising:

provm a top plate assembly seated on a top surface of a bottom plate with a continuous spacer seated on the top surface of the bottom plate between the top plate assembly and the bottom plate to define a molding space;

providing a first reservoir that provides a first receptacle for containing fluid and defining a through slot in a bottom surface of the reservoir, the through slot extending across the first receptacle and being in fluid communication with a channel defined by the first reservoir above the through slot and between the through slot and the molding space, the channel being in fluid communication with the molding space;

providing a second reservoir having a substantially planar base and a body extending from the base to provide a second receptacle for containing fluid, the base being connected to the central plate forming an array bottom, the array bottom defining a plurality of sample wells and traversing the central plate, the samples wells providing fluid communication between the second receptacle and the molding space;

introducing a sufficient volume of gel-forming material into first receptacle, the through slot, the channel, the molding space and the plurality of sample wells, substantially filling the wells;

inserting a mating comb into the plurality of sample wells to displace the gel-forming material;

polymerizing the gel-forming material;

removing the mating comb from the plurality of sample loading wells.

* * * * *